United States Patent
Zhou et al.

(10) Patent No.: US 12,090,227 B2
(45) Date of Patent: Sep. 17, 2024

(54) METHOD TO IMPROVE THE ENCAPSULATION EFFICIENCY AND PHYSICOCHEMICAL STABILITY OF GINSENOSIDES RG3 AND CK NANO-EMULSION

(71) Applicants: Jiangnan University, Wuxi (CN); Standard Foods (China) Co., Ltd, Suzhou (CN); Le Bonta Wellness Co., Ltd, Shanghai (CN)

(72) Inventors: Peng Zhou, Wuxi (CN); Changshu Liu, Suzhou (CN); Yaowei Liu, Wuxi (CN); Tao Yang, Wuxi (CN); Yan Zheng, Wuxi (CN); Jianguo Liu, Suzhou (CN); Kexin Li, Shanghai (CN); Shuyan Lu, Shanghai (CN)

(73) Assignees: JIANGNAN UNIVERSITY, Wuxi (CN); STANDARD FOODS (CHINA) CO., LTD, Suzhou (CN); LE BONTA WELLNESS CO., LTD, Shanghai (CN)

( * ) Notice: Subject to any disclaimer, the term of this patent is extended or adjusted under 35 U.S.C. 154(b) by 0 days.

(21) Appl. No.: 18/526,168

(22) Filed: Dec. 1, 2023

(65) Prior Publication Data
US 2024/0099972 A1    Mar. 28, 2024

Related U.S. Application Data

(63) Continuation of application No. PCT/CN2023/101753, filed on Jun. 21, 2023.

(30) Foreign Application Priority Data

Jul. 22, 2022 (CN) .......................... 202210867114.0

(51) Int. Cl.
| | | |
|---|---|---|
| A61K 9/00 | (2006.01) |
| A61K 9/107 | (2006.01) |
| A61K 31/7028 | (2006.01) |
| A61K 47/26 | (2006.01) |
| A61K 47/42 | (2017.01) |
| A61K 47/44 | (2017.01) |

(52) U.S. Cl.
CPC ........ A61K 9/1075 (2013.01); A61K 31/7028 (2013.01); A61K 47/26 (2013.01); A61K 47/42 (2013.01); A61K 47/44 (2013.01)

(58) Field of Classification Search
CPC .............. A61K 9/1075; A61K 31/7028; A61K 47/26; A61K 47/42; A61K 47/44; A61K 9/107; A61K 31/704; A61K 47/12; A23L 2/38; A23L 33/125; A61P 3/10; A61P 9/00; A61P 25/00; A61P 29/00; A61P 35/00; A61P 37/02; A61P 39/00; A61P 39/06; A23V 2002/00
See application file for complete search history.

(56) References Cited

FOREIGN PATENT DOCUMENTS

| CN | 105296587 A | 2/2016 |
|---|---|---|
| CN | 107456472 A | 12/2017 |
| CN | 110037296 A | 7/2019 |
| CN | 114432263 A | 5/2022 |
| CN | 115120559 A | 9/2022 |

OTHER PUBLICATIONS

Gomes et al. (Colloids and Surfaces B: Biointerfaces 164 (2018) 272-280).*
Hou et al. (Food Bioscience 31 (2019) 100427).*
Ganesan et al. (RSC Adv. 2015, 5,98634).*
Food Sci. Biotechnol. 19(3): 647-653 (2010)).*
T.P.Sari et. al. "preparation and characterization of naoemulsion encapsulating curcumin" Food Hydrocolloids, V 43, Jan. 31, 2025, 540-546.

* cited by examiner

*Primary Examiner* — Michael G. Hartley
*Assistant Examiner* — Melissa J Perreira
(74) *Attorney, Agent, or Firm* — IPRO, PLLC

(57) ABSTRACT

The present disclosure relates to a method to improve the encapsulation efficiency and physicochemical stability of ginsenosides Rg3 and CK nano-emulsion, belonging to the field of functional emulsions. The method to improve the encapsulation efficiency and physicochemical stability of ginsenosides Rg3 and CK nano-emulsion, includes the following steps: (1) WPI, Tween 80 and water were mixed evenly according to the amount ratio of 0.5 g:0.5-0.7 g:50 mL to obtain the aqueous phase; (2) Mixing a saponin extract containing the minor ginsenosides Rg3 and CK with edible oil evenly to obtain the oil phase; (3) Mixing the aqueous phase with the oil phase, carrying out shearing dispersion to obtain coarse emulsion, and then allowing the coarse emulsion to be subjected to microfluidization homogenization to obtain an oil-in-water nano-emulsion containing the minor ginsenosides Rg3 and CK. The nano-emulsion of the disclosure has a high encapsulation efficiency of Rg3 and CK, good physicochemical stability during storage, freeze-thaw cycles, heating, and other industrial treatments, which could be used to improve the bioavailability of minor ginsenoside Rg3 and CK.

7 Claims, 6 Drawing Sheets

Storage for 0d   Storage for 28d

WPI

WPC

METHOD TO IMPROVE THE ENCAPSULATION EFFICIENCY AND PHYSICOCHEMICAL STABILITY OF GINSENOSIDES RG3 AND CK NANO-EMULSION

TECHNICAL FIELD

The present disclosure relates to a method to improve the encapsulation efficiency and physicochemical stability of ginsenosides Rg3 and CK nano-emulsion, belonging to the field of functional emulsions.

BACKGROUND

Ginsenosides are triterpenoid compounds composed of hydrophobic aglycones with low polarity and hydrophilic glycosyls with high polarity. Ginsenosides are the major bioactive substances in *ginseng*, and have various physiological functions, like anti-senility, anti-tumor, anti-inflammation, oxidation resistance, fatigue resistance, anti-diabetes, regulating body immunity, protecting nervous system and cardiovascular system. According to the difference in abundance in wild *ginseng*, ginsenosides can be divided into major ginsenosides and minor ginsenosides. The major ginsenosides contain more glycosyls, and constitute nearly 80-90% of the total ginsenosides in *ginseng*; however, they have a low bioavailability after oral intake owing to its large molecular size and poor permeability through the cell membrane. In contrast, the deglycosylated minor ginsenosides are quite rare in wild *ginseng*, but are easily absorbed into the bloodstream from the gastrointestinal tract, functioning as true bioactive compounds. Therefore, how to efficiently obtain these minor ginsenosides, such as Rg3 and CK, is an urgent problem that needs to be solved.

In addition, although the minor ginsenosides Rg3 and CK have stronger pharmacological activities, their water solubility is extremely poor, which limits the bioavailability of ginsenosides Rg3 and CK by oral administration. For natural bioactive substances with poor water solubility, the preparation of nano-emulsion delivery system is the most common method to improve their bioavailability. For example, patent CN110037296A discloses a preparation method of whey protein isolate-based ginsenoside nano-emulsion, in which a ginsenoside Rg3 pure product is used for preparing ginsenoside nano-emulsion by an ultrasonic homogenization technology, but the prepared nano-emulsion has poor stability and low encapsulation efficiency, which is not conducive to its storage and further production and processing.

SUMMARY

Technical Problem

The existing nano-emulsion prepared with minor ginsenosides has poor stability and low encapsulation efficiency, which is not conducive to its storage and further production and processing.

Technical Solution

In order to solve the above-mentioned problem, according to the present disclosure, minor ginsenosides Rg3 and CK are firstly extracted by acid hydrolysis at high temperatures, and then a nano-emulsion is prepared using edible oil and the obtained saponin extract containing the ginsenosides Rg3 and CK as an oil phase, and a mixture of whey protein isolate (WPI) solution and Tween 80 as an aqueous phase. The nano-emulsion of the present disclosure is milky white, has a nano-scale particle size, and shows a good physicochemical stability and high encapsulation efficiency of minor ginsenosides, which can be used to improve the bioavailability of ginsenosides Rg3 and CK, and conforms to actual industrial application demands, thus having a good market prospect.

The purpose of the present disclosure is to provide a method to improve the encapsulation efficiency and physicochemical stability of ginsenosides Rg3 and CK nano-emulsion, including the following steps:

(1) Aqueous Phase:

Mixing WPI, Tween 80 and water evenly to obtain the aqueous phase;

(2) Oil Phase:

Mixing a saponin extract containing the minor ginsenosides Rg3 and CK with edible oil evenly to obtain the oil phase;

(3) Preparation of Nano-Emulsion:

Mixing the aqueous phase with the oil phase, carrying out shearing dispersion to obtain coarse emulsion, and then allowing the coarse emulsion to be subjected to microfluidization homogenization to obtain an oil-in-water nano-emulsion containing the minor ginsenosides Rg3 and CK.

In one implementation of the present disclosure, the amount ratio of WPI, Tween 80 and water in step (1) is 0.5 g:(0.5-0.7) g:50 mL.

In one implementation of the present disclosure, in step (1), a preparation method of the aqueous phase described is as follows: dissolving WPI in water, heating at 80-90° C. for 15-20 min, then immediately cooling to room temperature (25±2° C.) with an ice water bath, then adding Tween 80, stirring at 200-400 rpm for 2-4 h, and finally standing still at 4° C. for 10-12 h until the product is completely hydrated, so as to obtain the aqueous phase.

In one implementation of the present disclosure, in step (2), a preparation method of the saponin extract containing the minor ginsenosides Rg3 and CK described includes the following steps:

Mixing *ginseng* tablets with a citric acid solution with a pH value of 1-7, and then heating the obtained mixture at 130° C. for 1-5 h to obtain the saponin extract containing the minor ginsenosides Rg3 and CK, where the amount ratio of the *ginseng* tablets to the citric acid solution is 1 g:(5-10) mL; and the extraction conditions in the method for extracting the minor ginsenosides Rg3 and CK by acid hydrolysis are as follows: heating extraction is carried out at 130° C. for 1 h when pH value is 2.0, or heating extraction is carried out at 130° C. for 3-5 h when pH value is 3.0-7.0.

In one implementation of the present disclosure, in step (2), the volume ratio of the saponin extract containing the minor ginsenosides Rg3 and CK to the edible oil is 4:1.

In one implementation of the present disclosure, in step (2), the edible oil includes one or more of rapeseed oil, soybean oil, sunflower seed oil, and peanut oil, etc.

In one implementation of the present disclosure, in step (2), the mixing involves stirring at 200-400 rpm for 10-12 h.

In one implementation of the present disclosure, in step (3), the volume ratio of the aqueous phase to the oil phase is 1:1.

In one implementation of the present disclosure, in step (3), the shearing dispersion involves shearing at 15000-18000 rpm for 4-6 min.

In one implementation of the present disclosure, in step (3), the microfluidization homogenization involves cycle homogenization at 600-800 bar for 10-15 min, with an applicable sample volume of 150-200 mL.

The second purpose of the present disclosure is the oil-in-water nano-emulsion containing the minor ginsenosides Rg3 and CK prepared by the method of the present disclosure.

The third purpose of the present disclosure is application of the oil-in-water nano-emulsion containing the minor ginsenosides Rg3 and CK in the fields of preparation of beverages and functional emulsions, etc.

In one implementation of the present disclosure, the functional emulsions include cosmetics and functional food.

In one implementation of the present disclosure, the preparation of beverages is to use the oil-in-water emulsion containing minor ginsenosides Rg3 and CK as raw and auxiliary materials for the application in the mixing stage of beverage production, with an amount of 30-60%, which can enhance the immune function of the beverages.

In one implementation of the present disclosure, the preparation of the functional emulsions is to use the oil-in-water emulsion containing minor ginsenosides Rg3 and CK as raw and auxiliary materials for the application in the mixing stage of the production of emulsion cosmetics, with an amount of 1-10%, which can enhance the whitening and skin care effects of the cosmetics.

[Beneficial Effects]

(1) Whey protein isolate (WPI), a by-product of cheese processing, is nutritious, easy to digest, and high in commercial value, and possesses surfactant properties, electrostatic and hydrophobic interactions, and appropriate steric conformation. When the WPI is used as an emulsifier to prepare a nano-emulsion delivery system, the ginsenosides Rg3 and CK obtained from acid hydrolysis by citric acid can be encapsulated in nano-emulsion, thereby improving the bioavailability of the ginsenosides Rg3 and CK. In the process of preparing the nano-emulsion delivery system containing the ginsenosides Rg3 and CK by using the WPI, Tween 80 is added, which not only enhances the physicochemical stability of the nano-emulsion, but also improves the encapsulation efficiency of the ginsenosides Rg3 and CK.

(2) The nano-emulsion prepared according to the present disclosure not only has a higher encapsulation efficiency of ginsenosides Rg3 and CK, but also has stronger processing stability in thermal sterilization, storage, and freeze-thaw cycles, will not cause stratification and other undesirable phenomena, and has longer shelf life and practical value.

Figure 2A:
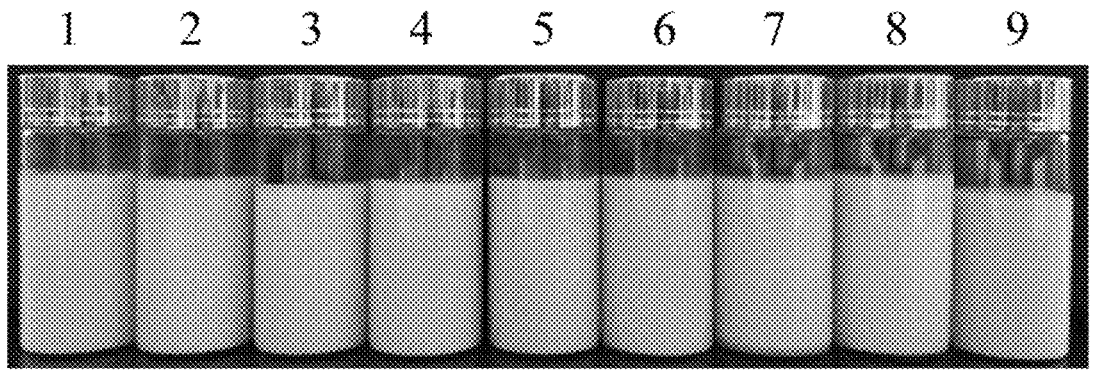
FIG. 2A shows photographs of oil-in-water nano-emulsion of Example 2 stored at 4° C. for 0 day. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2B:
FIG. 2B shows photographs of oil-in-water nano-emulsion of Example 2 stored at 25° C. for 0 day. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2C:
FIG. 2C shows photographs of oil-in-water nano-emulsion of Example 2 stored at 4° C. for 7 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2D:
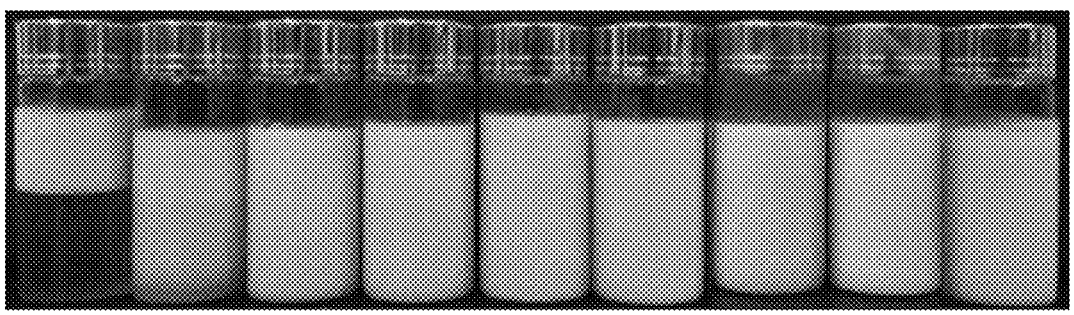
FIG. 2D shows photographs of oil-in-water nano-emulsion of Example 2 stored at 25° C. for 7 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2E:
FIG. 2E shows photographs of oil-in-water nano-emulsion of Example 2 stored at 4° C. for 14 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2F:
FIG. 2F shows photographs of oil-in-water nano-emulsion of Example 2 stored at 25° C. for 14 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2G:
FIG. 2G shows photographs of oil-in-water nano-emulsion of Example 2 stored at 4° C. for 21 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2H:
FIG. 2H shows photographs of oil-in-water nano-emulsion of Example 2 stored at 25° C. for 21 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween.
Figure 2I:
FIG. 2I shows photographs of oil-in-water nano-emulsion of Example 2 stored at 4° C. for 28 days. 1: 0.5% WPI; 2: 0.5% WPI+0.1% Tween; 3: 0.5% WPI+0.2% Tween; 4.
Figure 2J:
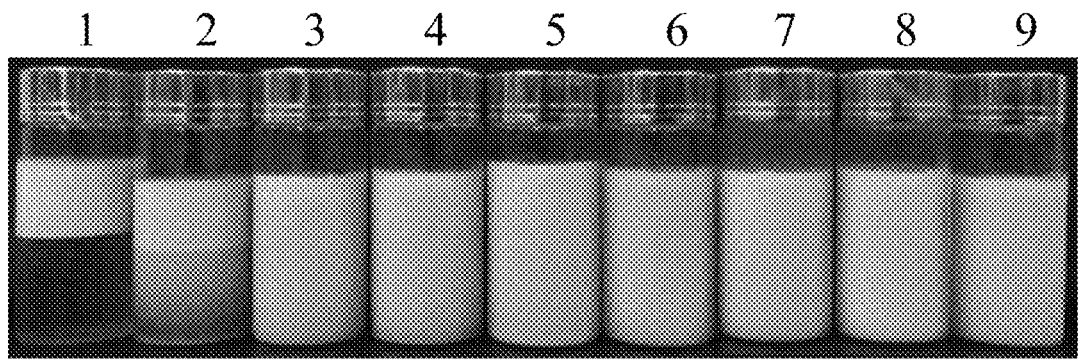
Figure 3:
Figure 3:
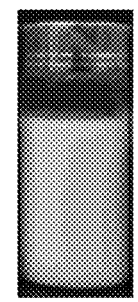
Figure 3:
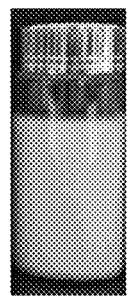
Figure 3:
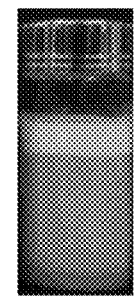

0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween;

FIG. 2J shows photographs of oil-in-water nano-emulsion of Example 2 stored at 25° C. for 28 days. 1: 0.5% WPI; 2: 0.5% WPI+0.1% Tween; 3: 0.5% WPI+0.2% Tween; 4: 0.5% WPI+0.3% Tween; 5: 0.5% WPI+0.4% Tween; 6: 0.5% WPI+0.5% Tween; 7: 0.5% WPI+0.6% Tween; 8: 0.5% WPI+0.7% Tween; 9: 0.5% Tween;

FIG. 3 is a schematic diagram presenting the storage of oil-in-water nano-emulsions of Example 2 and Comparative Example 14.

DETAILED DESCRIPTION

The exemplary examples of the present disclosure are described below, and it should be understood that the examples are for the purpose of better illustrating the present disclosure and are not intended to limit it.

Test Method

1. Yield Test:

The obtained saponin extract containing minor ginsenosides Rg3 and CK was allowed to pass through a 0.45 µm filter membrane to remove impurities therein, and the concentrations ($C_{Rg3}$ and $C_{CK}$) of the ginsenosides Rg3 and CK in the saponin extract containing the minor ginsenosides Rg3 and CK were determined by high performance liquid chromatography (with an elution procedure shown in Table 1).

TABLE 1

Elution procedure of high performance liquid chromatography

| Time (min) | Acetonitrile (%) | Milli-Q water (%) |
|---|---|---|
| 0 | 22.0 | 78.0 |
| 25.00 | 22.0 | 78.0 |
| 35.00 | 32.5 | 67.5 |
| 65.00 | 34.0 | 66.0 |
| 66.00 | 42.0 | 58.0 |
| 114.00 | 98.0 | 2.0 |
| 119.00 | 98.0 | 2.0 |
| 120.00 | 22.0 | 78.0 |
| 130.00 | 22.0 | 78.0 |

The yields of the ginsenosides Rg3 and CK were calculated in equations (1) and (2), respectively.

$$\text{Yields of the ginsenosides } Rg3 = C_{Rg3} \times V/m \quad (1)$$

$$\text{Yields of the ginsenosides } CK = C_{CK} \times V/m \quad (2)$$

Where, V is the volume (mL) of a citric acid solution, and m is the mass (g) of *ginseng* tablets.

2. Encapsulation Efficiency Test:

The saponin extract containing the minor ginsenosides Rg3 and CK was obtained under the optimal acid hydrolysis conditions of citric acid, and then the impurities in the extract were removed through a 0.45 µm filter membrane; and the concentrations ($C_{Rg3}$ and $C_{CK}$) of the ginsenosides Rg3 and CK in the saponin extract containing the minor ginsenosides Rg3 and CK were determined by high performance liquid chromatography (with an elution procedure shown in Table 1).

The oil-in-water nano-emulsion was centrifuged at 4° C. for 30 min at a speed of 35000 g, which divided into three layers, where the top layer was milky white grease, the middle layer was a clear and transparent aqueous phase, and the bottom was precipitate; the middle layer was allowed to pass through a 0.45 µm filter membrane to remove impurities therein, and the concentrations of free ginsenosides Rg3 and CK ($C_{Rg3}'$ and $C_{CK}'$) in the oil-in-water nano-emulsion were determined by high performance liquid chromatography (with an elution procedure shown in Table 1); and the encapsulation efficiency of ginsenosides Rg3 and CK in the nano-emulsion were calculated in equations (3) and (4), respectively.

$$\text{Encapsulation efficiency of ginsenosides } Rg3 = (1 - C_{Rg3}'/40\% \ C_{Rg3}) \times 100\% \quad (3)$$

$$\text{Encapsulation efficiency of ginsenosides } CK = (1 - C_{CK}'/40\% \ C_{CK}) \times 100\% \quad (4)$$

3. Test for Centrifugal Stability Constant:

The oil-in-water nano-emulsion was diluted 100 times with Milli-Q water, and the absorbance value ($A_0$) was measured at 490 nm by an ultraviolet-visible spectrophotometer after mixing. The oil-in-water nano-emulsion was centrifuged at 4° C. for 15 min at a speed of 4000 rpm, the subnatant was diluted 100 times with Milli-Q water, and the absorbance value ($A_0'$) was measured at 490 nm by an ultraviolet-visible spectrophotometer after mixing; and the centrifugal stability constant of the nano-emulsion was calculated in equation (5).

$$\text{Centrifugal stability constant of the nano-emulsion} = A_0'/A_0 \times 100\% \quad (5)$$

4. Test for Mean Droplet Diameter:

The oil-in-water nano-emulsion was diluted 300 times with Milli-Q water, and the mean droplet diameter of the nano-emulsion was determined with a particle size analyzer (the refractive indices of water and nano-emulsion were 1.33 and 1.46, respectively).

5. Test for Polydispersity Index:

The oil-in-water nano-emulsion was diluted 300 times with Milli-Q water, and the polydispersity index of the nano-emulsion was determined with a particle size analyzer (the refractive indices of water and nano-emulsion were 1.33 and 1.46, respectively).

6. Test for Turbidity:

The oil-in-water nano-emulsion was diluted 100 times with Milli-Q water, the absorbance value (A) was measured at 650 nm by an ultraviolet-visible spectrophotometer after mixing, and the turbidity of the nano-emulsion was calculated in equation (6).

$$\text{Turbidity of the nano-emulsion} = 2.303 \times A \times D/I \quad (6)$$

Where, D is the coefficient of dilution (100), and I is the path length of a cuvette (cm).

7. Storage Experiment:

The oil-in-water nano-emulsion was stored at 4° C. and 25° C. for 4 weeks, respectively. The mean droplet diameter, polydispersity index, centrifugal stability constant and turbidity of the nano-emulsion were determined weekly, and the appearance of the nano-emulsion was photographed once a week.

8. Freeze-Thaw Cycle Experiment:

The oil-in-water nano-emulsion was stored at −18° C. for 22 h, then thawed at 40° C. for 2 h, and a freeze-thaw cycle was performed 2 times. The mean droplet diameter, polydispersity index, centrifugal stability constant and turbidity of the nano-emulsion were determined.

9. Thermal Sterilization Treatment:

The oil-in-water nano-emulsion was respectively heated at 40° C., 65° C. and 90° C. for 30 min, and then cooled to room temperature (25±2° C.). The mean droplet diameter, polydispersity index, centrifugal stability constant and turbidity of the nano-emulsion were determined.

Example 1

A method to prepare a saponin extract containing minor ginsenosides Rg3 and CK includes the following steps:

10 g of *ginseng* tablets were mixed with 100 mL of citric acid solutions with pH values of 1.0, 2.0, 3.0, and 7.0, and the obtained mixtures were heated at 50° C., 70° C., 90° C., and 130° C. for 1 h, 3 h, and 5 h, respectively, so that the saponin extract containing the minor ginsenosides Rg3 and CK was obtained.

The obtained saponin extract containing the minor ginsenosides Rg3 and CK was tested. The test results are shown in FIG. 1A-FIG. 1H.

Figure 1A:
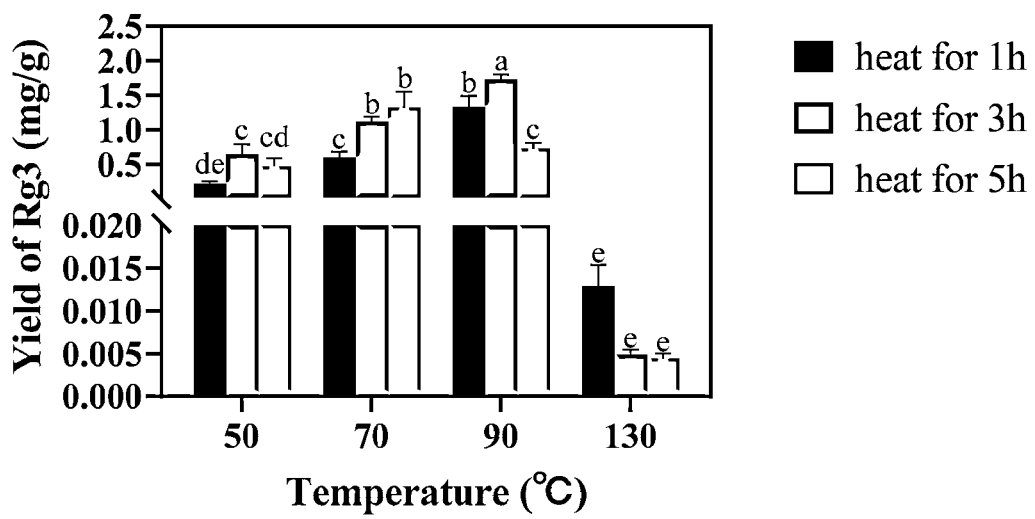
FIG. 1A shows the test results of the yield of minor ginsenoside Rg3 in a saponin extract obtained from Example 1 by heating at reaction temperatures of 50° C., 70° C., 90° C., and 130° C. for 1 h, 3 h, and 5 h when pH value is 1.0.
Figure 1B:
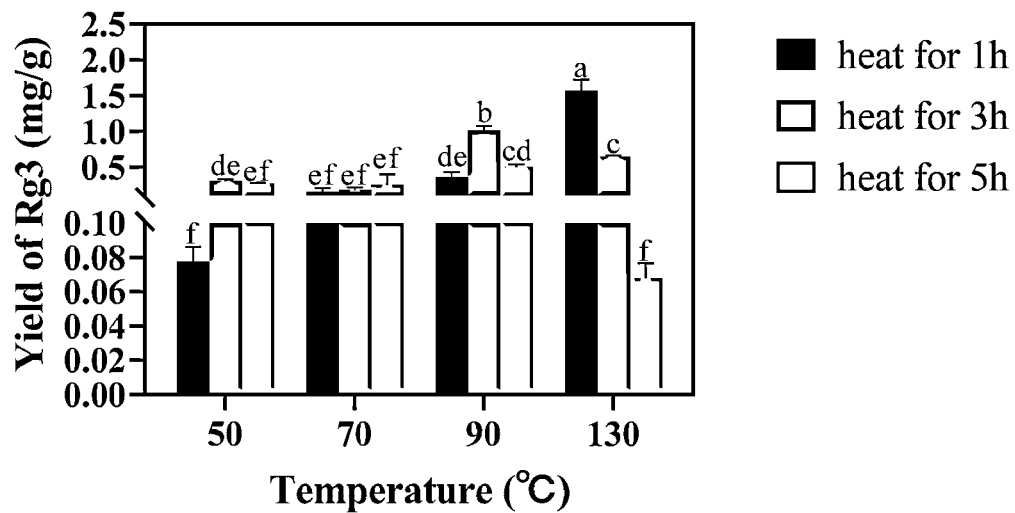
FIG. 1B shows the test results of the yield of minor ginsenoside Rg3 in a saponin extract obtained from Example 1 by heating at reaction temperatures of 50° C., 70° C., 90° C., and 130° C. for 1 h, 3 h, and 5 h when pH value is 2.0.
Figure 1C:
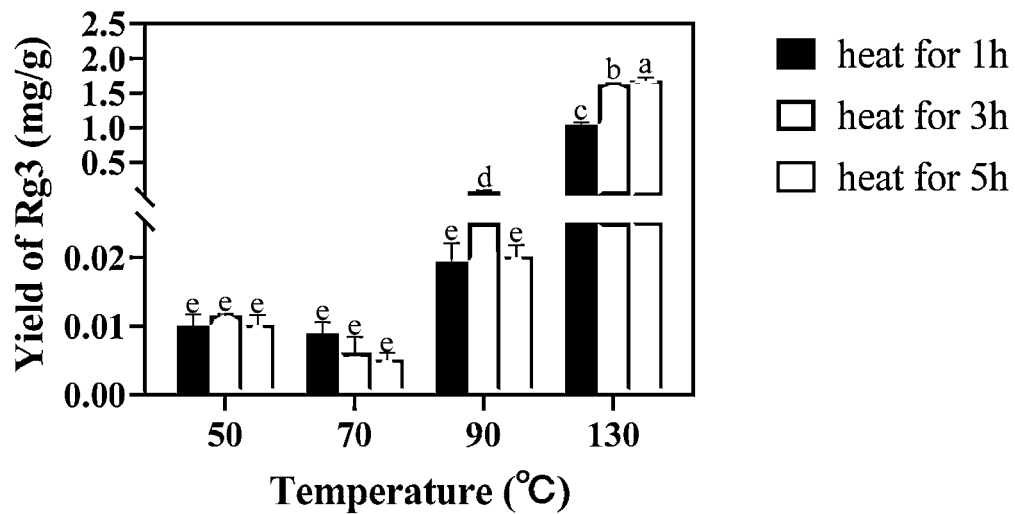
FIG. 1C shows the test results of the yield of minor ginsenoside Rg3 in a saponin extract obtained from Example 1 by heating at reaction temperatures of 50° C., 70° C., 90° C., and 130° C. for 1 h, 3 h, and 5 h when pH value is 3.0.
Figure 1D:
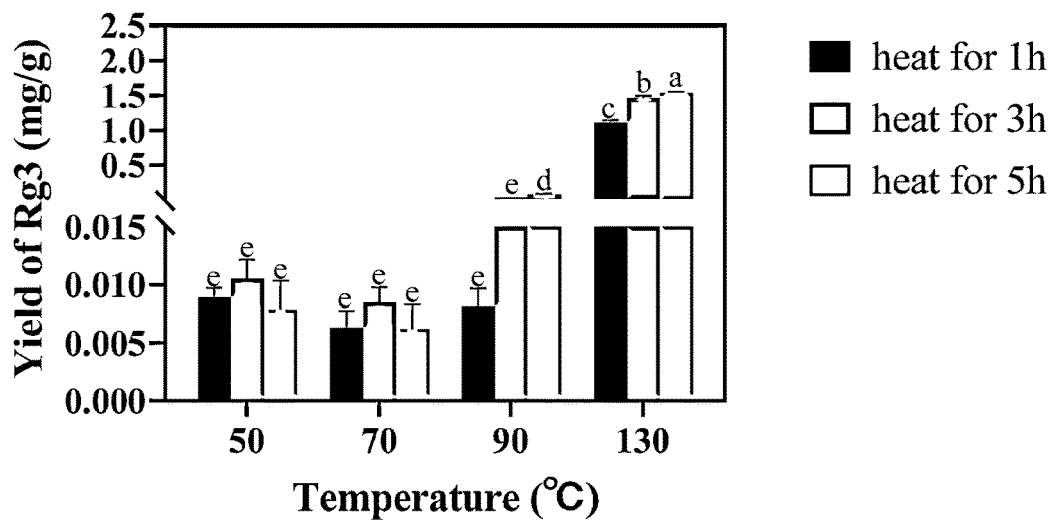
FIG. 1D shows the test results of the yield of minor ginsenoside Rg3 in a saponin extract obtained from Example 1 by heating at reaction temperatures of 50° C., 70° C., 90° C., and 130° C. for 1 h, 3 h, and 5 h when pH value is 7.0.
Figure 1E:
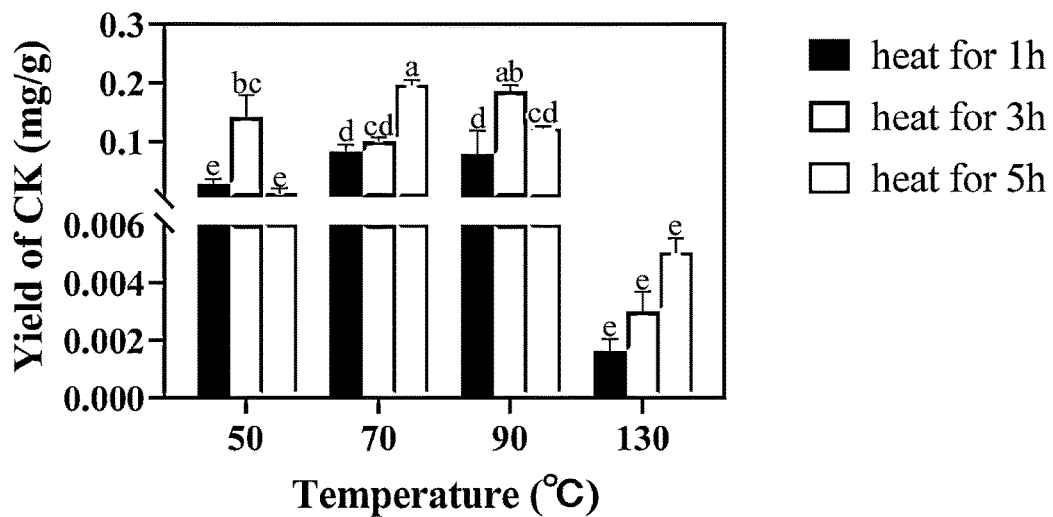
FIG. 1E shows the test results of the yield of minor ginsenoside CK in a saponin extract obtained from Example 1 by heating at reaction temperatures of 50° C., 70° C., 90° C., and 130° C. for 1 h, 3 h, and 5 h when pH value is 1.0.
Figure 1F:
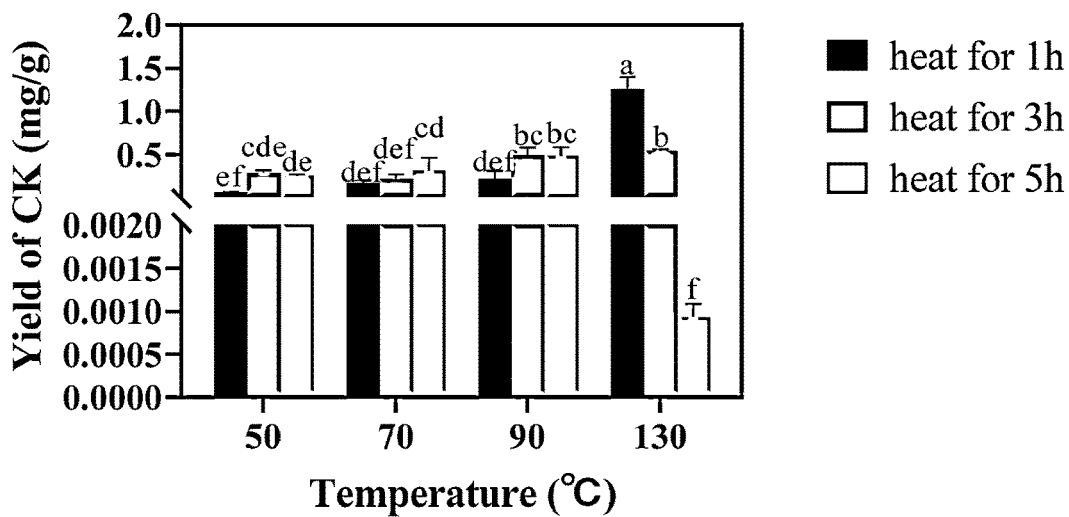
FIG. 1F shows the test results of the yield of minor ginsenoside CK in a saponin extract obtained from Example 1 by heating at reaction temperatures of 50° C., 70° C., 90° C., and 130° C. for 1 h, 3 h, and 5 h when pH value is 2.0.
Figure 1G:
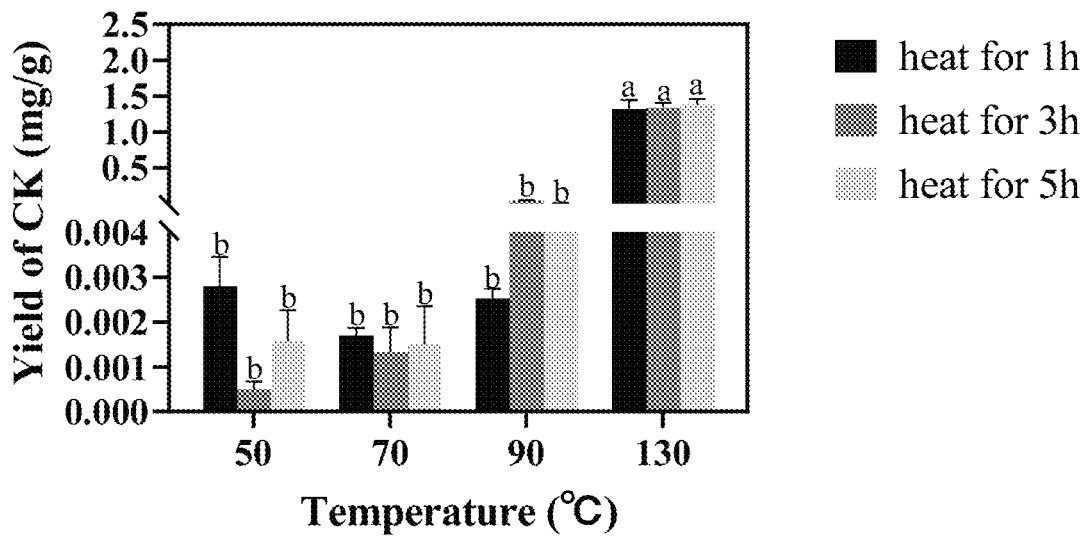
FIG. 1G shows the test results of the yield of minor ginsenoside CK in a saponin extract obtained from Example 1 by heating at reaction temperatures of 50° C., 70° C., 90° C., and 130° C. for 1 h, 3 h, and 5 h when pH value is 3.0.
Figure 1H:
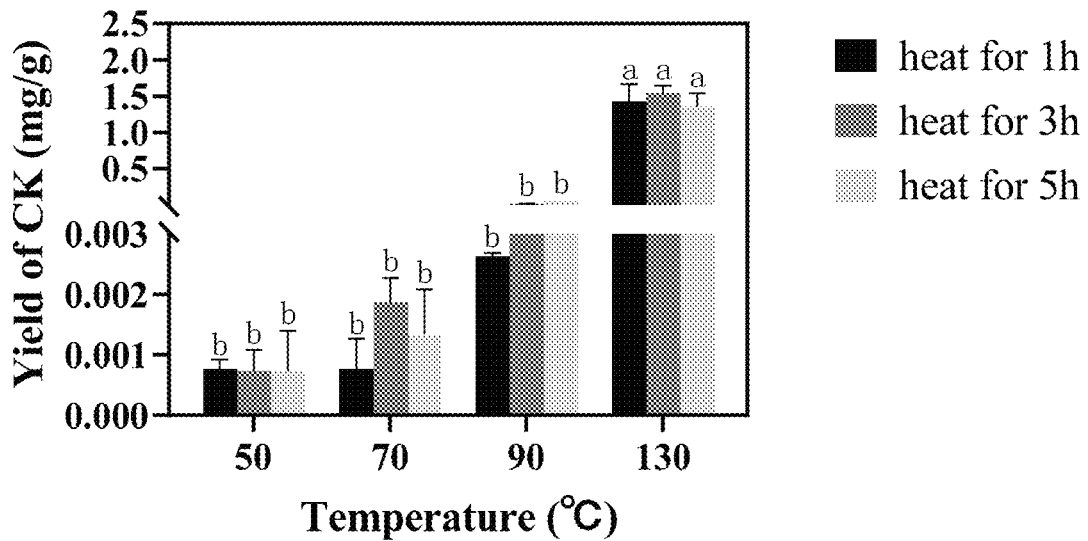
FIG. 1H shows the test results of the yield of minor ginsenoside CK in a saponin extract obtained from Example 1 by heating at reaction temperatures of 50° C., 70° C., 90° C., and 130° C. for 1 h, 3 h, and 5 h when pH value is 7.0.

According to statistical analysis, the pH value of a citric acid solution, the heating temperature and the heating time had interactive effects on the yield of ginsenosides Rg3 and CK. When the pH value of the citric acid solution was 1.0, the yield of the ginsenosides Rg3 and CK first increased and then decreased with the increase of heating temperature (as shown by FIG. 1A and FIG. 1E), which might be due to the combination of extremely low pH value and high temperature promoting the conversion of major ginsenosides to Rg3 and CK. When the pH value of the citric acid solution was 2.0, the yield of the ginsenosides Rg3 and CK increased with the increase of heating temperature (as shown by FIG. 1B and FIG. 1F). Under this condition, the combination of acid and heating had a positive effect on the yield of the ginsenosides Rg3 and CK. When the pH value of the citric acid solution was 3.0 and 7.0, the yield of the ginsenosides Rg3 and CK did not change significantly with the increase of heating temperature under heating of the ginsenosides Rg3 and CK at 50° C., 70° C. and 90° C., while the yield of the ginsenosides Rg3 and CK significantly increased under heating at 130° C.

It could be seen from FIG. 1A-FIG. 1H that the acid hydrolysis condition for the highest yield of ginsenoside Rg3 was: heating at 90° C. for 3 h when pH value was 1.0; and the acid hydrolysis conditions for the highest yield of ginsenoside CK was: heating at 130° C. for 3 h when pH value was 7.0. The optimal acid hydrolysis conditions were: heating at 130° C. for 1 h when pH value was 2.0, heating at 130° C. for 3 h or 5 h when pH value was 3.0, and heating at 130° C. for 3 h or 5 h when pH value was 7.0. Under these conditions, the ginsenosides Rg3 and CK and their respective highest yields (1.73±0.07 mg/g and 1.54±0.11 mg/g) had no significant difference.

Example 2

A method to improve the encapsulation efficiency and physicochemical stability of ginsenosides Rg3 and CK nano-emulsion includes the following steps:

(1) Aqueous Phase:

WPI was dissolved in water and heated at 80° C. for 15 min, the product was immediately cooled to room temperature (25±2° C.) with an ice water bath, Tween 80 was then added, the obtained mixture was stirred at 200 rpm for 2 h, and finally, the product was allowed to stand still at 4° C. for 12 h until being completely hydrated, so as to obtain the aqueous phase, where the amount ratio of WPI, Tween 80, and water was 0.5 g:0.5 g:50 mL.

(2) Oil Phase:

A saponin extract containing minor ginsenosides Rg3 and CK (heated at 130° C. for 1 h when pH value was 2.0) and sunflower seed oil were mixed according to a volume ratio of 4:1 and evenly stirred at 200 rpm for 12 h to obtain the oil phase.

(3) Preparation of Nano-Emulsion:

The aqueous phase and the oil phase were mixed according to a volume ratio of 1:1, and shearing dispersion was performed on the obtained mixture at a speed of 15000 rpm for 5 min, so that coarse emulsion was obtained; and after that, the coarse emulsion was subjected to microfluidization homogenization under the pressure of 600 bar for 10 min to obtain the oil-in-water nano-emulsion.

Example 3

The amount ratio of WPI, Tween 80 and water in step (1) of Example 2 was adjusted to 0.5 g:0.6 g:50 mL, and the other steps were the same as those in Example 2, so as to obtain oil-in-water nano-emulsion.

Example 4

The amount ratio of WPI, Tween 80 and water in step (1) of Example 2 was adjusted to 0.5 g:0.7 g:50 mL, and the other steps were the same as those in Example 2, so as to obtain oil-in-water nano-emulsion.

Comparative Example 1

In step (1) of example 2 was omitted Tween 80, the amount ratio of WPI, Tween 80 and water in step (1) was adjusted to 0.5 g:0 g:50 mL, and the other steps were the same as those in Example 2, so as to obtain oil-in-water nano-emulsion.

Comparative Example 2

The amount ratio of WPI, Tween 80 and water in step (1) of Example 2 was adjusted to 0.5 g:0.1 g:50 mL, and the other steps were the same as those in Example 2, so as to obtain oil-in-water nano-emulsion.

Comparative Example 3

The amount ratio of WPI, Tween 80 and water in step (1) of Example 2 was adjusted to 0.5 g:0.2 g:50 mL, and the other steps were the same as those in Example 2, so as to obtain oil-in-water nano-emulsion.

Comparative Example 4

The amount ratio of WPI, Tween 80 and water in step (1) of Example 2 was adjusted to 0.5 g:0.3 g:50 mL, and the other steps were the same as those in Example 2, so as to obtain oil-in-water nano-emulsion.

Comparative Example 5

The amount ratio of WPI, Tween 80 and water in step (1) of Example 2 was adjusted to 0.5 g:0.4 g:50 mL, and the other steps were the same as those in Example 2, so as to obtain oil-in-water nano-emulsion.

Comparative Example 6

In step (1) of example 2 was omitted WPI, the amount ratio of WPI, Tween 80 and water in step (1) was adjusted to 0 g:0.5 g:50 mL, and the other steps were the same as those in Example 2, so as to obtain oil-in-water nano-emulsion.

The obtained oil-in-water nano-emulsions was tested for performances, and the test results are as follows:

The encapsulation efficiency of bioactive compounds and the centrifugal stability constant of an emulsion are the most important indices to evaluate the performances of the emulsion. The encapsulation efficiency of the ginsenosides Rg3 and CK is an index to evaluate the encapsulation effect of the emulsion, and the centrifugal stability constant is a common index to evaluate the stability of the emulsion during storage. For an emulsion delivery system, the higher the encapsulation efficiency of a bioactive substance and centrifugal stability constant are, the better the performances of the emulsion are. The mean droplet diameter, polydispersity index and turbidity are indices to evaluate the stability of an emulsion. The smaller the mean droplet diameter is, the more stable the emulsion is; the smaller the polydispersity index is, the better the uniformity of the emulsion droplet size is; and the turbidity is related to the mean droplet diameter, which is an indirect index reflecting the stability of the emulsion.

Table 2 shows the performance test results of the oil-in-water nano-emulsions. It could be seen from Table 2 that in the nano-emulsions prepared by mixing WPI and Tween 80, with the increase of the amount of Tween 80, the encapsulation efficiency of ginsenosides Rg3 and CK and the centrifugal stability constant of the nano-emulsions increased continuously, and then tended to be stable; and the mean droplet diameter, polydispersity index and turbidity of the nano-emulsions decreased continuously, and then tended to be stable. The nano-emulsion prepared by WPI alone had a lower centrifugal stability constant, while the nano-emulsion prepared by Tween 80 alone had a lower encapsulation efficiency of ginsenosides Rg3 and CK.

The experimental results show that when the amount ratio of WPI, Tween 80 and water is 0.5 g:(0.5-0.7) g:50 mL, the mean droplet diameter, polydispersity index and turbidity of the nano-emulsions were smaller, and thus the nano-emulsions had a higher encapsulation efficiency (Rg3: 81.21-81.34%; CK: 83.31-83.44%) and stronger stability (53.13-53.56%).

The obtained oil-in-water nano-emulsions were subjected to storage experiments, and the performances of the nano-emulsions were tested. The test results are as follows:

Photographs of the nano-emulsions stored at 4° C. and 25° C. are shown in FIG. 2A-FIG. 2J. It could be seen from FIG. 2A-FIG. 2J that under the conditions of 4° C. and 25° C., the appearance of all fresh nano-emulsions is uniform on the first day, but the nano-emulsions gradually appeared stratification with the extension of storage time. Whether at 4° C. or 25° C., the nano-emulsions prepared with 0.5 g of WPI or 0.1 g of Tween 80 alone showed stratification after storage for 7 days, and the stratification of the nano-emulsions stored at 25° C. was more severe than that of the nano-emulsions stored at 4° C. (as shown by FIG. 2C and FIG. 2D). In addition, the lower the centrifugal stability constant is, the earlier the stratification of the nano-emulsions occurs. Under the conditions of 4° C. and 25° C., the ginsenoside nano-emulsions prepared with 0.5 g of WPI and more than 0.2 g of Tween 80 or 0.3 g of Tween 80 alone did not show obvious stratification even after 28 days of storage.

Table 3-Table 10 show the performance test results of the oil-in-water nano-emulsions after the storage experiments. It could be seen from Table 3-Table 10 that whether at 4° C. or 25° C., the mean droplet diameter and polydispersity index of the nano-emulsions gradually increased with the extension of storage time. The mean droplet diameter and polydispersity index of the nano-emulsions stored at 25° C. increased more rapidly compared with the nano-emulsions stored at 4° C. With the increase of the amount of Tween 80, the increase degree of the mean droplet diameter and polydispersity index of the nano-emulsions decreased, and then tended to be stable, indicating that the higher the amount of Tween 80 was, the stronger the storage stability of the nano-emulsions was.

Whether at 4° C. or 25° C., the centrifugal stability constant and turbidity of the nano-emulsions decreased gradually with the extension of storage time. The centrifugal stability constant and turbidity of the nano-emulsions stored at 25° C. decreased more rapidly compared with the nano-

TABLE 2

The performance test results of the oil-in-water nano-emulsions

| Example | Encapsulation efficiency of ginsenosides Rg3 | Encapsulation efficiency of ginsenosides CK | Mean droplet diameter(nm) | Polydispersity index | Centrifugal stability constant | Turbidity ($cm^{-1}$) |
|---|---|---|---|---|---|---|
| Example 2 | 81.34 ± 0.10%$^a$ | 83.44 ± 0.30%$^a$ | 310.87 ± 1.45$^f$ | 0.17 ± 0.02$^d$ | 53.56 ± 0.48%$^a$ | 328.41 ± 7.09$^f$ |
| Example 3 | 81.21 ± 0.44%$^a$ | 83.31 ± 0.33%$^a$ | 308.28 ± 0.35$^f$ | 0.16 ± 0.00$^d$ | 53.29 ± 0.31%$^a$ | 319.03 ± 4.16$^f$ |
| Example 4 | 81.24 ± 0.45%$^a$ | 83.34 ± 0.45%$^a$ | 305.67 ± 0.42$^f$ | 0.15 ± 0.00$^d$ | 53.13 ± 0.44%$^a$ | 315.86 ± 2.44$^f$ |
| Comparative Example 1 | 70.93 ± 0.19%$^f$ | 72.34 ± 0.43%$^f$ | 814.65 ± 2.11$^a$ | 0.28 ± 0.00$^a$ | 3.74 ± 0.27%$^e$ | 567.61 ± 7.74$^a$ |
| Comparative Example 2 | 72.97 ± 0.11%$^e$ | 74.41 ± 0.18%$^e$ | 739.84 ± 1.53$^b$ | 0.26 ± 0.01$^{ab}$ | 13.46 ± 0.15%$^d$ | 521.55 ± 4.06$^b$ |
| Comparative Example 3 | 75.07 ± 0.43%$^d$ | 76.35 ± 0.17%$^d$ | 647.96 ± 5.85$^c$ | 0.24 ± 0.01$^{bc}$ | 33.40 ± 2.50%$^c$ | 480.48 ± 2.46$^c$ |
| Comparative Example 4 | 77.23 ± 0.24%$^c$ | 78.61 ± 0.27%$^c$ | 469.99 ± 2.49$^d$ | 0.23 ± 0.00$^c$ | 40.69 ± 1.38%$^b$ | 398.80 ± 9.98$^d$ |
| Comparative Example 5 | 79.75 ± 0.08%$^b$ | 81.36 ± 0.22%$^b$ | 345.17 ± 4.11$^e$ | 0.22 ± 0.01$^c$ | 43.10 ± 1.42%$^b$ | 367.71 ± 20.87$^e$ |
| Comparative Example 6 | 63.42 ± 0.54%$^g$ | 65.02 ± 0.14%$^g$ | 261.81 ± 1.76$^g$ | 0.11 ± 0.01$^e$ | 40.12 ± 1.03%$^b$ | 413.00 ± 4.87$^d$ |

Note:
Different letters of the same index indicated that there were significant differences ($p < 0.05$).

emulsions stored at 4° C. With the increase of the amount of Tween 80, the decrease degree of the centrifugal stability constant and turbidity of the nano-emulsions decreased, and then tended to be stable, indicating that the higher the amount of Tween 80 was, the stronger the storage stability of the nano-emulsions was.

The experimental results show that in the process of the storage experiment, when the amount ratio of WPI, Tween 80 and water is 0.5 g:(0.5-0.7) g:50 mL, the mean droplet diameter, polydispersity index, centrifugal stability constant and turbidity of the nano-emulsions were changed less, and thus the nano-emulsions had stronger storage stability.

TABLE 3

The performance (the mean droplet diameter(nm)) test results of the oil-in-water nano-emulsions stored at 4° C.

| Example | 0 d | 7 d | 14 d | 21 d | 28 d |
|---|---|---|---|---|---|
| Example 2 | 310.87 ± 1.45$^a$ | 313.24 ± 1.47$^a$ | 320.32 ± 3.19$^a$ | 326.44 ± 2.24$^a$ | 331.74 ± 1.13$^a$ |
| Example 3 | 308.28 ± 0.35$^a$ | 312.22 ± 0.28$^a$ | 317.16 ± 0.23a | 321.05 ± 1.69$^a$ | 328.10 ± 0.43$^a$ |
| Example 4 | 305.67 ± 0.42$^a$ | 309.05 ± 0.23$^a$ | 314.20 ± 0.09$^a$ | 318.94 ± 0.01$^a$ | 324.17 ± 0.29$^a$ |
| Comparative Example 1 | 814.65 ± 2.11$^e$ | 1019.67 ± 33.82$^d$ | 1179.14 ± 45.01$^c$ | 1425.17 ± 26.04$^b$ | 1939.15 ± 41.74$^a$ |
| Comparative Example2 | 739.84 ± 1.53$^e$ | 792.95 ± 3.89$^d$ | 942.85 ± 2.15$^c$ | 1106.03 ± 56.07$^b$ | 1445.97 ± 44.34$^a$ |
| Comparative Example3 | 647.96 ± 5.85$^e$ | 718.62 ± 6.32$^d$ | 826.23 ± 2.63$^c$ | 955.31 ± 3.06$^b$ | 1052.14 ± 23.12$^a$ |
| Comparative Example4 | 469.99 ± 2.49$^d$ | 527.27 ± 4.20$^c$ | 548.33 ± 6.67$^b$ | 594.49 ± 1.23$^b$ | 684.92 ± 5.03$^a$ |
| Comparative Example5 | 345.17 ± 4.11$^c$ | 375.87 ± 2.73$^b$ | 398.35 ± 0.71$^b$ | 403.46 ± 2.65a$^b$ | 445.74 ± 1.91$^a$ |
| Comparative Example6 | 261.81 ± 1.76$^a$ | 263.65 ± 0.24$^a$ | 265.88 ± 2.24$^a$ | 268.33 ± 1.89$^a$ | 275.81 ± 0.50$^a$ |

Note:
Different letters of the same index indicated that there were significant differences (p < 0.05).

TABLE 4

The performance (the polydispersity index) test results of the oil-in-water nano-emulsions stored at 4° C.

| Example | 0 d | 7 d | 14 d | 21 d | 28 d |
|---|---|---|---|---|---|
| Example 2 | 0.17 ± 0.02$^c$ | 0.19 ± 0.01$^{bc}$ | 0.21 ± 0.00$^b$ | 0.24 ± 0.01$^a$ | 0.25 ± 0.00$^a$ |
| Example 3 | 0.16 ± 0.00$^d$ | 0.18 ± 0.00$^c$ | 0.20 ± 0.00$^b$ | 0.21 ± 0.00$^a$ | 0.23 ± 0.00$^a$ |
| Example 4 | 0.15 ± 0.00$^d$ | 0.17 ± 0.00$^{cd}$ | 0.19 ± 0.00$^c$ | 0.20 ± 0.00$^b$ | 0.21 ± 0.00$^a$ |
| Comparative Example 1 | 0.28 ± 0.00$^c$ | 0.30 ± 0.01$^c$ | 0.31 ± 0.01$^{bc}$ | 0.34 ± 0.01$^b$ | 0.36 ± 0.01$^a$ |
| Comparative Example2 | 0.26 ± 0.01$^c$ | 0.29 ± 0.00$^c$ | 0.30 ± 0.00$^{bc}$ | 0.32 ± 0.00$^{ab}$ | 0.34 ± 0.01$^a$ |
| Comparative Example3 | 0.24 ± 0.01$^c$ | 0.25 ± 0.01$^{bc}$ | 0.27 ± 0.01$^b$ | 0.29 ± 0.01$^a$ | 0.32 ± 0.00$^a$ |
| Comparative Example4 | 0.23 ± 0.00$^c$ | 0.24 ± 0.00$^{bc}$ | 0.25 ± 0.00$^b$ | 0.28 ± 0.01$^a$ | 0.30 ± 0.00$^a$ |
| Comparative Example5 | 0.22 ± 0.01$^c$ | 0.23 ± 0.01$^{bc}$ | 0.24 ± 0.01$^b$ | 0.26 ± 0.01$^a$ | 0.27 ± 0.00$^a$ |
| Comparative Example6 | 0.11 ± 0.01$^c$ | 0.13 ± 0.00$^c$ | 0.16 ± 0.01$^b$ | 0.18 ± 0.01$^b$ | 0.20 ± 0.01$^a$ |

Note:
Different letters of the same index indicated that there were significant differences (p < 0.05).

TABLE 5

The performance (the centrifugal stability constant) test results of the oil-in-water nano-emulsions stored at 4° C.

| Example | 0 d | 7 d | 14 d | 21 d | 28 d |
|---|---|---|---|---|---|
| Example 2 | 53.56 ± 0.48%$^a$ | 52.06 ± 0.42%$^b$ | 49.86 ± 0.66%$^c$ | 46.96 ± 0.25%$^d$ | 43.36 ± 0.34%$^e$ |
| Example 3 | 53.29 ± 0.31%$^a$ | 52.21 ± 0.43%$^b$ | 49.84 ± 0.15%$^b$ | 48.36 ± 0.04%$^c$ | 44.36 ± 0.06%$^d$ |
| Example 4 | 53.13 ± 0.44%$^a$ | 52.21 ± 0.11%$^a$ | 50.18 ± 0.47%$^b$ | 48.98 ± 0.15%$^b$ | 44.81 ± 0.16%$^c$ |
| Comparative Example 1 | 3.74 ± 0.27%$^a$ | 0.44 ± 0.04%$^b$ | 0.34 ± 0.10%$^b$ | 0.34 ± 0.10%$^b$ | 0.34 ± 0.10%$^b$ |
| Comparative Example2 | 13.46 ± 0.15%$^a$ | 10.36 ± 0.10%$^b$ | 5.56 ± 0.20%$^c$ | 0.36 ± 0.08%$^d$ | 0.36 ± 0.07%$^d$ |
| Comparative Example3 | 33.40 ± 2.50%$^a$ | 31.09 ± 0.45%$^b$ | 26.69 ± 0.56%$^c$ | 20.59 ± 0.71%$^d$ | 12.79 ± 0.30%$^e$ |
| Comparative Example4 | 40.69 ± 1.38%$^a$ | 38.39 ± 0.26%$^b$ | 34.79 ± 0.26%$^c$ | 29.89 ± 0.26%$^d$ | 23.69 ± 0.71%$^e$ |

TABLE 5-continued

The performance (the centrifugal stability constant) test
results of the oil-in-water nano-emulsions stored at 4° C.

| Example | 0 d | 7 d | 14 d | 21 d | 28 d |
|---|---|---|---|---|---|
| Comparative Example5 | 43.10 ± 1.42%$^a$ | 41.20 ± 0.37%$^b$ | 38.30 ± 0.74%$^c$ | 34.40 ± 0.45%$^d$ | 29.50 ± 0.41%$^e$ |
| Comparative Example6 | 40.12 ± 1.03%$^a$ | 38.12 ± 0.38%$^b$ | 35.02 ± 0.29%$^c$ | 31.02 ± 0.36%$^d$ | 26.02 ± 0.17%$^e$ |

Note:
Different letters of the same index indicated that there were significant differences ($p < 0.05$).

TABLE 6

The performance (turbidity($cm^{-1}$)) test results of the oil-in-water nano-emulsions stored at 4° C.

| Example | 0 d | 7 d | 14 d | 21 d | 28 d |
|---|---|---|---|---|---|
| Example 2 | 328.41 ± 7.09$^a$ | 321.41 ± 7.59$^{ab}$ | 307.41 ± 7.08$^b$ | 286.41 ± 7.24$^c$ | 258.41 ± 6.65$^d$ |
| Example 3 | 319.03 ± 4.16$^a$ | 315.70 ± 2.44$^a$ | 307.70 ± 1.88$^a$ | 286.36 ± 1.10$^b$ | 259.03 ± 2.98$^c$ |
| Example 4 | 315.86 ± 2.44$^a$ | 310.19 ± 1.34$^a$ | 302.19 ± 3.13$^a$ | 281.86 ± 2.28$^b$ | 259.19 ± 3.66$^c$ |
| Comparative Example 1 | 567.61 ± 7.74$^a$ | 538.61 ± 1.26$^b$ | 480.61 ± 5.62$^c$ | 393.61 ± 6.95$^d$ | 277.61 ± 5.32$^e$ |
| Comparative Example2 | 521.55 ± 4.06$^a$ | 497.55 ± 4.49$^b$ | 449.55 ± 6.20$^c$ | 377.55 ± 7.63$^d$ | 281.55 ± 3.82$^e$ |
| Comparative Example3 | 480.48 ± 2.46$^a$ | 459.48 ± 6.24$^b$ | 417.48 ± 1.70$^c$ | 354.48 ± 5.55$^d$ | 270.48 ± 9.47$^e$ |
| Comparative Example4 | 398.80 ± 9.98$^a$ | 382.80 ± 5.23$^b$ | 350.80 ± 2.55$^c$ | 302.80 ± 7.32$^d$ | 238.80 ± 7.26$^a$ |
| Comparative Example5 | 367.71 ± 20.87$^a$ | 356.71 ± 4.34$^a$ | 334.71 ± 8.80$^b$ | 301.71 ± 5.73$^c$ | 257.71 ± 4.88$^d$ |
| Comparative Example6 | 413.00 ± 4.87$^a$ | 400.00 ± 7.72$^a$ | 374.00 ± 10.17$^b$ | 335.00 ± 7.61$^c$ | 283.00 ± 7.78$^d$ |

Note:
Different letters of the same index indicated that there were significant differences ($p < 0.05$).

TABLE 7

The performance (the mean droplet diameter(nm)) test results
of the oil-in-water nano-emulsions stored at 25° C.

| Example | 0 d | 7 d | 14 d | 21 d | 28 d |
|---|---|---|---|---|---|
| Example 2 | 310.87 ± 1.45$^a$ | 337.13 ± 3.00$^a$ | 367.52 ± 4.17$^a$ | 409.02 ± 1.24$^b$ | 416.35 ± 4.27$^b$ |
| Example 3 | 308.28 ± 0.35$^a$ | 331.88 ± 2.81$^a$ | 361.53 ± 2.33$^a$ | 395.87 ± 3.19$^b$ | 402.69 ± 0.82$^c$ |
| Example 4 | 305.67 ± 0.42$^a$ | 326.24 ± 1.03$^a$ | 351.78 ± 0.29$^a$ | 383.69 ± 0.91$^b$ | 394.65 ± 2.57$^c$ |
| Comparative Example 1 | 814.65 ± 2.11$^a$ | 1164.45 ± 17.02$^b$ | 1476.74 ± 82.77$^c$ | 1735.83 ± 87.81$^d$ | 2130.16 ± 115.10$^e$ |
| Comparative Example 2 | 739.84 ± 1.53$^a$ | 974.53 ± 2.84$^b$ | 1046.54 ± 37.55$^c$ | 1275.69 ± 59.61$^d$ | 1671.29 ± 70.52$^e$ |
| Comparative Example 3 | 647.96 ± 5.85$^a$ | 861.09 ± 4.86$^b$ | 971.21 ± 1.69$^c$ | 1073.28 ± 8.43$^d$ | 1196.66 ± 81.03$^e$ |
| Comparative Example 4 | 469.99 ± 2.49$^a$ | 624.85 ± 4.41$^b$ | 685.01 ± 1.20$^{bc}$ | 732.92 ± 7.44$^{cd}$ | 772.82 ± 6.00$^d$ |
| Comparative Example 5 | 345.17 ± 4.11$^a$ | 465.12 ± 2.38$^b$ | 483.31 ± 2.37$^{bc}$ | 519.88 ± 2.88$^{bc}$ | 538.47 ± 3.51$^c$ |
| Comparative Example 6 | 261.81 ± 1.76$^a$ | 271.95 ± 0.88$^a$ | 278.14 ± 1.09$^a$ | 280.34 ± 2.23$^a$ | 287.29 ± 5.13$^a$ |

Note:
Different letters of the same index indicated that there were significant differences ($p < 0.05$).

TABLE 8

The performance (the polydispersity index) test results
of the oil-in-water nano-emulsions stored at 25° C.

| Example | 0 d | 7 d | 14 d | 21 d | 28 d |
|---|---|---|---|---|---|
| Example 2 | 0.17 ± 0.02$^c$ | 0.21 ± 0.00$^b$ | 0.23 ± 0.00$^b$ | 0.25 ± 0.01$^a$ | 0.27 ± 0.00$^a$ |
| Example 3 | 0.16 ± 0.00$^c$ | 0.19 ± 0.00$^b$ | 0.21 ± 0.01$^b$ | 0.23 ± 0.00$^a$ | 0.24 ± 0.00$^a$ |
| Example 4 | 0.15 ± 0.00$^c$ | 0.18 ± 0.01$^b$ | 0.20 ± 0.00$^b$ | 0.22 ± 0.00$^a$ | 0.24 ± 0.00$^a$ |
| Comparative Example 1 | 0.28 ± 0.00$^d$ | 0.32 ± 0.00$^c$ | 0.34 ± 0.01$^{bc}$ | 0.36 ± 0.01$^b$ | 0.39 ± 0.01$^a$ |

TABLE 8-continued

The performance (the polydispersity index) test results
of the oil-in-water nano-emulsions stored at 25° C.

| Example | 0 d | 7 d | 14 d | 21 d | 28 d |
|---|---|---|---|---|---|
| Comparative Example 2 | $0.26 \pm 0.01^d$ | $0.30 \pm 0.01^c$ | $0.32 \pm 0.00^{bc}$ | $0.34 \pm 0.01^b$ | $0.36 \pm 0.01^a$ |
| Comparative Example 3 | $0.24 \pm 0.01^d$ | $0.28 \pm 0.01^c$ | $0.30 \pm 0.01^{bc}$ | $0.32 \pm 0.00^b$ | $0.35 \pm 0.00^a$ |
| Comparative Example 4 | $0.23 \pm 0.00^d$ | $0.25 \pm 0.00^{cd}$ | $0.27 \pm 0.00^c$ | $0.30 \pm 0.00^b$ | $0.34 \pm 0.01^a$ |
| Comparative Example 5 | $0.22 \pm 0.01^c$ | $0.24 \pm 0.00^c$ | $0.26 \pm 0.01^b$ | $0.28 \pm 0.01^a$ | $0.30 \pm 0.00^a$ |
| Comparative Example 6 | $0.11 \pm 0.01^c$ | $0.15 \pm 0.00^c$ | $0.16 \pm 0.01^b$ | $0.20 \pm 0.01^b$ | $0.21 \pm 0.00^a$ |

Note:
Different letters of the same index indicated that there were significant differences ($p < 0.05$).

TABLE 9

The performance (the centrifugal stability constant) test
results of the oil-in-water nano-emulsions stored at 25° C.

| Example | 0 d | 7 d | 14 d | 21 d | 28 d |
|---|---|---|---|---|---|
| Example 2 | $53.56 \pm 0.48\%^a$ | $51.56 \pm 0.52\%^b$ | $48.56 \pm 0.51\%^c$ | $44.56 \pm 0.38\%^d$ | $39.56 \pm 0.38\%^e$ |
| Example 3 | $53.29 \pm 0.31\%^a$ | $52.14 \pm 0.45\%^a$ | $50.14 \pm 0.15\%^b$ | $45.26 \pm 0.03\%^c$ | $40.26 \pm 0.05\%^d$ |
| Example 4 | $53.13 \pm 0.44\%^a$ | $52.15 \pm 0.37\%^a$ | $50.48 \pm 0.41\%^b$ | $45.58 \pm 0.32\%^c$ | $40.38 \pm 0.19\%^d$ |
| Comparative Example 1 | $3.74 \pm 0.27\%^a$ | $0.24 \pm 0.10\%^b$ | $0.24 \pm 0.05\%^b$ | $0.24 \pm 0.04\%^b$ | $0.24 \pm 0.09\%^b$ |
| Comparative Example 2 | $13.46 \pm 0.15\%^a$ | $9.46 \pm 0.74\%^b$ | $2.46 \pm 0.43\%^c$ | $0.46 \pm 0.11\%^d$ | $0.26 \pm 0.08\%^d$ |
| Comparative Example 3 | $33.40 \pm 2.50\%^a$ | $30.29 \pm 0.33\%^b$ | $24.29 \pm 0.65\%^c$ | $15.79 \pm 0.34\%^d$ | $4.79 \pm 0.39\%^e$ |
| Comparative Example 4 | $40.69 \pm 1.38\%^a$ | $37.69 \pm 0.24\%^b$ | $32.69 \pm 0.44\%^c$ | $25.69 \pm 0.43\%^d$ | $16.69 \pm 0.65\%^e$ |
| Comparative Example 5 | $43.10 \pm 1.42\%^a$ | $40.60 \pm 0.28\%^b$ | $36.60 \pm 0.40\%^c$ | $31.10 \pm 0.22\%^d$ | $24.10 \pm 0.48\%^e$ |
| Comparative Example 6 | $40.12 \pm 1.03\%^a$ | $37.82 \pm 0.61\%^b$ | $34.32 \pm 0.50\%^c$ | $29.62 \pm 0.47\%^d$ | $23.72 \pm 0.58\%^e$ |

Note:
Different letters of the same index indicated that there were significant differences ($p < 0.05$).

TABLE 10

The performance (turbidity($cm^{-1}$)) test results of the
oil-in-water nano-emulsions stored at 25° C.

| Example | 0 d | 7 d | 14 d | 21 d | 28 d |
|---|---|---|---|---|---|
| Example 2 | $328.41 \pm 7.09^a$ | $318.41 \pm 1.83^a$ | $298.41 \pm 4.13^b$ | $268.41 \pm 4.38^c$ | $228.41 \pm 3.07^d$ |
| Example 3 | $319.03 \pm 4.16^a$ | $313.20 \pm 2.07^a$ | $291.53 \pm 1.76^b$ | $270.70 \pm 0.59^c$ | $230.70 \pm 0.94^d$ |
| Example 4 | $315.86 \pm 2.44^a$ | $308.69 \pm 1.67^a$ | $290.02 \pm 3.64^b$ | $267.52 \pm 1.49^c$ | $230.86 \pm 4.76^d$ |
| Comparative Example 1 | $567.61 \pm 7.74^a$ | $532.61 \pm 3.18^b$ | $462.61 \pm 4.45^c$ | $357.61 \pm 4.70^d$ | $217.61 \pm 5.48^e$ |
| Comparative Example 2 | $521.55 \pm 4.06^a$ | $491.55 \pm 3.61^b$ | $431.55 \pm 5.03^c$ | $341.55 \pm 4.28^d$ | $221.55 \pm 4.07^e$ |
| Comparative Example 3 | $480.48 \pm 2.46^a$ | $455.48 \pm 2.54^b$ | $405.48 \pm 3.82^c$ | $330.48 \pm 1.68^d$ | $230.48 \pm 4.15^e$ |
| Comparative Example 4 | $398.80 \pm 9.98^a$ | $378.80 \pm 4.26^b$ | $338.80 \pm 1.43^c$ | $278.80 \pm 5.91^d$ | $208.80 \pm 3.62^e$ |
| Comparative Example 5 | $367.71 \pm 20.87^a$ | $352.71 \pm 2.37^b$ | $322.71 \pm 3.48^c$ | $277.71 \pm 4.09^d$ | $217.71 \pm 5.89^e$ |
| Comparative Example 6 | $413.00 \pm 4.87^a$ | $395.50 \pm 1.99^b$ | $360.50 \pm 4.81^c$ | $308.00 \pm 2.81^d$ | $238.00 \pm 5.98^e$ |

Note:
Different letters of the same index indicated that there were significant differences ($p < 0.05$).

The obtained oil-in-water nano-emulsions were subjected to a freeze-thaw cycle experiment, and the performances of the nano-emulsions were tested. The test results are as follows:

Table 11-Table 14 show the performance test results of the oil-in-water nano-emulsions after the freeze-thaw cycle experiment. It could be seen from Table 11-Table 14 that the mean droplet diameter and polydispersity index of the nano-emulsions increased with the increase of freeze-thaw cycles. With the increase of the amount of Tween 80, the increase degree of the mean droplet diameter and polydispersity index of the nano-emulsions decreased, and then tended to be stable, indicating that the higher the amount of Tween 80 was, the stronger the freeze-thaw stability of the nano-emulsions was.

With the increase of the freeze-thaw cycles, the centrifugal stability constant and turbidity of the nano-emulsions decreased. With the increase of the amount of Tween 80, the decrease degree of the centrifugal stability constant and turbidity of the nano-emulsions decreased, and then tended to be stable, indicating that the higher the amount of Tween 80 was, the stronger the freeze-thaw stability of the nano-emulsions was.

The experimental results show that in the process of the freeze-thaw cycle experiment, when the amount ratio of WPI, Tween 80 and water is 0.5 g:(0.5-0.7) g:50 mL, the mean droplet diameter, polydispersity index, centrifugal stability constant and turbidity of the nano-emulsions were changed less, and thus the nano-emulsions had higher freeze-thaw stability.

TABLE 11

The performance (the mean droplet diameter (nm)) test results of the oil-in-water nano-emulsions after the freeze-thaw cycle experiment.

| Example | New emulsion | First freeze-thaw cycles | Second freeze-thaw cycles |
|---|---|---|---|
| Example 2 | $310.87 \pm 1.45^a$ | $313.22 \pm 1.14^a$ | $325.95 \pm 2.21^a$ |
| Example 3 | $308.28 \pm 0.35^a$ | $313.15 \pm 0.48^a$ | $324.30 \pm 1.11^a$ |
| Example 4 | $305.67 \pm 0.42^a$ | $312.29 \pm 0.62^a$ | $320.81 \pm 3.34^a$ |
| Comparative Example 1 | $814.65 \pm 2.11^a$ | $1304.19 \pm 50.66^b$ | $1909.43 \pm 47.65^c$ |
| Comparative Example 2 | $739.84 \pm 1.53^a$ | $3174.34 \pm 62.63^b$ | $5231.81 \pm 45.97^c$ |
| Comparative Example 3 | $647.96 \pm 5.85^a$ | $1639.80 \pm 18.53^b$ | $2092.79 \pm 4.71^c$ |
| Comparative Example 4 | $469.99 \pm 2.49^a$ | $540.46 \pm 6.45^b$ | $582.21 \pm 3.36^c$ |
| Comparative Example 5 | $345.17 \pm 4.11^a$ | $380.83 \pm 1.82^b$ | $468.93 \pm 5.60^b$ |
| Comparative Example 6 | $261.81 \pm 1.76^a$ | $277.95 \pm 1.50^a$ | $284.45 \pm 2.06^a$ |

Note:
Different letters of the same index indicated that there were significant differences (p < 0.05).

TABLE 12

The performance (the polydispersity index) test results of the oil-in-water nano-emulsions after the freeze-thaw cycle experiment

| Example | New emulsion | First freeze-thaw cycle | Second freeze-thaw cycle |
|---|---|---|---|
| Example 2 | $0.17 \pm 0.02^b$ | $0.22 \pm 0.00^a$ | $0.26 \pm 0.01^a$ |
| Example 3 | $0.16 \pm 0.00^b$ | $0.21 \pm 0.00^a$ | $0.24 \pm 0.01^a$ |
| Example 4 | $0.15 \pm 0.00^b$ | $0.20 \pm 0.00^a$ | $0.23 \pm 0.00^a$ |
| Comparative Example 1 | $0.28 \pm 0.00^c$ | $0.35 \pm 0.01^b$ | $0.43 \pm 0.00^a$ |
| Comparative Example 2 | $0.26 \pm 0.01^c$ | $0.46 \pm 0.01^b$ | $0.53 \pm 0.01^a$ |
| Comparative Example 3 | $0.24 \pm 0.01^c$ | $0.30 \pm 0.01^b$ | $0.33 \pm 0.00^a$ |
| Comparative Example 4 | $0.23 \pm 0.00^b$ | $0.30 \pm 0.00^a$ | $0.31 \pm 0.00^a$ |
| Comparative Example 5 | $0.22 \pm 0.01^b$ | $0.27 \pm 0.00^a$ | $0.29 \pm 0.01^a$ |
| Comparative Example 6 | $0.11 \pm 0.01^c$ | $0.19 \pm 0.01^b$ | $0.23 \pm 0.01^a$ |

Note:
Different letters of the same index indicated that there were significant differences (p < 0.05).

TABLE 13

The performance (the centrifugal stability constant) test results of the oil-in-water nano-emulsions after the freeze-thaw cycle experiment

| Example | New emulsion | First freeze-thaw cycles | Second freeze-thaw cycles |
|---|---|---|---|
| Example 2 | $53.56 \pm 0.48\%^a$ | $47.11 \pm 0.42\%^b$ | $41.64 \pm 1.62\%^c$ |
| Example 3 | $53.29 \pm 0.31\%^a$ | $48.02 \pm 0.27\%^b$ | $41.74 \pm 0.02\%^c$ |
| Example 4 | $53.13 \pm 0.44\%^a$ | $48.38 \pm 0.34\%^b$ | $41.90 \pm 0.37\%^c$ |
| Comparative Example 1 | $3.74 \pm 0.27\%^a$ | $0.98 \pm 0.12\%^a$ | $0.49 \pm 0.05\%^a$ |
| Comparative Example 2 | $13.46 \pm 0.15\%^a$ | $6.44 \pm 0.37\%^b$ | $4.69 \pm 0.13\%^b$ |
| Comparative Example 3 | $33.40 \pm 2.50\%^a$ | $24.93 \pm 1.85\%^b$ | $17.44 \pm 3.82\%^c$ |
| Comparative Example 4 | $40.69 \pm 1.38\%^a$ | $28.93 \pm 0.09\%^b$ | $23.50 \pm 2.28\%^c$ |

TABLE 13-continued

The performance (the centrifugal stability constant) test results of the
oil-in-water nano-emulsions after the freeze-thaw cycle experiment

| Example | New emulsion | First freeze-thaw cycles | Second freeze-thaw cycles |
|---|---|---|---|
| Comparative Example 5 | 43.10 ± 1.42%$^a$ | 36.31 ± 1.06%$^b$ | 27.33 ± 3.09%$^c$ |
| Comparative Example 6 | 40.12 ± 1.03%$^a$ | 38.95 ± 0.58%$^{ab}$ | 34.52 ± 2.78%$^b$ |

Note:
Different letters of the same index indicated that there were significant differences ($p < 0.05$).

TABLE 14

The performance (turbidity($cm^{-1}$)) test results of the oil-in-
water nano-emulsions after the freeze-thaw cycle experiment.

| Example | New emulsion | First freeze-thaw cycles | Second freeze-thaw cycles |
|---|---|---|---|
| Example 2 | 328.41 ± 7.09$^a$ | 293.25 ± 10.81$^b$ | 278.28 ± 4.84$^b$ |
| Example 3 | 319.03 ± 4.16$^a$ | 296.08 ± 5.66$^b$ | 286.79 ± 3.57$^b$ |
| Example 4 | 315.86 ± 2.44$^a$ | 298.69 ± 2.96$^b$ | 288.79 ± 1.33$^b$ |
| Comparative Example 1 | 567.61 ± 7.74$^a$ | 495.07 ± 13.33$^b$ | 380.15 ± 5.11$^c$ |
| Comparative Example 2 | 521.55 ± 4.06$^a$ | 479.95 ± 6.39$^b$ | 368.02 ± 9.91$^c$ |
| Comparative Example 3 | 480.48 ± 2.46$^a$ | 437.57 ± 9.81$^b$ | 361.80 ± 5.19$^c$ |
| Comparative Example 4 | 398.80 ± 9.98$^a$ | 355.20 ± 10.06$^b$ | 341.69 ± 4.72$^b$ |
| Comparative Example 5 | 367.71 ± 20.87$^a$ | 325.72 ± 4.35$^b$ | 292.25 ± 2.53$^c$ |
| Comparative Example 6 | 413.00 ± 4.87$^a$ | 355.12 ± 4.79$^b$ | 326.64 ± 8.73$^c$ |

Note:
Different letters of the same index indicated that there were significant differences ($p < 0.05$).

The obtained oil-in-water nano-emulsions were subjected to a thermal sterilization treatment experiment, and the performances of the nano-emulsions were tested. The test results are as follows:

Table 15-Table 18 show the performance test results of the oil-in-water nano-emulsions after the thermal sterilization treatment experiment. It could be seen from Table 15-Table 18 that the mean droplet diameter and polydispersity index of the nano-emulsions increased with the increase of thermal treatment temperature. With the increase of the amount of Tween 80, the increase degree of the mean droplet diameter and polydispersity index of the nano-emulsions decreased, and then tended to be stable, indicating that the higher the amount of Tween 80 was, the stronger the thermal stability of the nano-emulsions was.

With the increase of the thermal treatment temperature, the centrifugal stability constant and turbidity of the nano-emulsions decreased. With the increase of the amount of Tween 80, the decrease degree of the centrifugal stability constant and turbidity of the nano-emulsions decreased, and then tended to be stable, indicating that the higher the amount of Tween 80 was, the stronger the thermal stability of the nano-emulsion was.

The experimental results show that in the process of the thermal treatment experiment, when the amount ratio of WPI, Tween 80 and water was 0.5 g:(0.5-0.7) g:50 mL, the mean droplet diameter, polydispersity index, centrifugal stability constant and turbidity of the nano-emulsions were changed less, and thus the nano-emulsions had stronger thermal stability.

TABLE 15

The performance (the mean droplet diameter(nm)) test results of the oil-in-
water nano-emulsions after the thermal sterilization treatment experiment

| Example | New emulsion | Heated at 40° C. for 30 min | Heated at 65° C. for 30 min | Heated at 90° C. for 30 min |
|---|---|---|---|---|
| Example 2 | 310.87 ± 1.45$^b$ | 313.00 ± 2.28$^b$ | 333.00 ± 2.94$^b$ | 512.17 ± 0.88$^a$ |
| Example 3 | 308.28 ± 0.35$^b$ | 312.61 ± 0.74$^b$ | 327.79 ± 2.48$^b$ | 500.34 ± 1.82$^a$ |
| Example 4 | 305.67 ± 0.42$^b$ | 309.96 ± 1.44$^b$ | 323.36 ± 1.01$^b$ | 481.57 ± 1.15$^a$ |
| Comparative Example 1 | 814.65 ± 2.11$^d$ | 2383.26 ± 29.78$^c$ | 2973.18 ± 107.72$^b$ | 5196.22 ± 61.38$^a$ |
| Comparative Example 2 | 739.84 ± 1.53$^d$ | 1686.25 ± 28.58$^c$ | 2205.71 ± 33.17$^b$ | 4373.34 ± 9.74$^a$ |
| Comparative Example 3 | 647.96 ± 5.85$^d$ | 1138.23 ± 28.90$^c$ | 1442.46 ± 28.97$^b$ | 2674.11 ± 32.32$^a$ |
| Comparative Example 4 | 469.99 ± 2.49$^d$ | 589.64 ± 4.27$^c$ | 778.48 ± 7.19$^b$ | 1077.83 ± 55.50$^a$ |
| Comparative Example 5 | 345.17 ± 4.11$^b$ | 363.57 ± 0.87$^b$ | 419.45 ± 3.37$^b$ | 616.26 ± 2.08$^a$ |
| Comparative Example 6 | 261.81 ± 1.76$^b$ | 277.51 ± 0.76$^{ab}$ | 287.04 ± 1.17$^{ab}$ | 348.09 ± 1.36$^a$ |

Note:
Different letters of the same index indicated that there were significant differences ($p < 0.05$).

TABLE 16

The performance (the polydispersity index) test results of the oil-in-water nano-emulsions after the thermal sterilization treatment experiment

| Example | New emulsion | Heated at 40° C. for 30 min | Heated at 65° C. for 30 min | Heated at 90° C. for 30 min |
|---|---|---|---|---|
| Example 2 | $0.17 \pm 0.02^d$ | $0.21 \pm 0.00^c$ | $0.23 \pm 0.00^b$ | $0.26 \pm 0.00^a$ |
| Example 3 | $0.16 \pm 0.00^d$ | $0.20 \pm 0.00^c$ | $0.21 \pm 0.00^b$ | $0.24 \pm 0.00^a$ |
| Example 4 | $0.15 \pm 0.00^d$ | $0.18 \pm 0.00^c$ | $0.20 \pm 0.00^b$ | $0.22 \pm 0.00^a$ |
| Comparative Example 1 | $0.28 \pm 0.00^d$ | $0.33 \pm 0.01^c$ | $0.39 \pm 0.01^b$ | $0.54 \pm 0.01^a$ |
| Comparative Example 2 | $0.26 \pm 0.01^d$ | $0.31 \pm 0.00^c$ | $0.36 \pm 0.01^b$ | $0.46 \pm 0.00^a$ |
| Comparative Example 3 | $0.24 \pm 0.01^d$ | $0.28 \pm 0.01^c$ | $0.33 \pm 0.00^b$ | $0.39 \pm 0.00^a$ |
| Comparative Example 4 | $0.23 \pm 0.00^d$ | $0.26 \pm 0.00^c$ | $0.30 \pm 0.00^b$ | $0.36 \pm 0.00^a$ |
| Comparative Example 5 | $0.22 \pm 0.01^d$ | $0.24 \pm 0.01^c$ | $0.27 \pm 0.00^b$ | $0.31 \pm 0.01^a$ |
| Comparative Example 6 | $0.11 \pm 0.01^d$ | $0.16 \pm 0.00^c$ | $0.18 \pm 0.00^b$ | $0.23 \pm 0.00^a$ |

Note:
Different letters of the same index indicated that there were significant differences ($p < 0.05$).

TABLE 17

The performance (the centrifugal stability constant) test results of the oil-in-water nano-emulsions after the thermal sterilization treatment experiment

| Example | New emulsion | Heated at 40° C. for 30 min | Heated at 65° C. for 30 min | Heated at 90° C. for 30 min |
|---|---|---|---|---|
| Example 2 | $53.56 \pm 0.48\%^a$ | $48.69 \pm 2.49\%^b$ | $33.03 \pm 1.27\%^c$ | $30.19 \pm 0.24\%^c$ |
| Example 3 | $53.29 \pm 0.31\%^a$ | $48.61 \pm 0.01\%^b$ | $34.39 \pm 0.02\%^c$ | $31.42 \pm 0.00\%^c$ |
| Example 4 | $53.13 \pm 0.44\%^a$ | $48.87 \pm 0.29\%^b$ | $35.59 \pm 0.05\%^c$ | $32.42 \pm 0.19\%^c$ |
| Comparative Example 1 | $3.74 \pm 0.27\%^a$ | $1.95 \pm 0.05\%^{ab}$ | $1.13 \pm 0.14\%^b$ | $0.60 \pm 0.02\%^b$ |
| Comparative Example 2 | $13.46 \pm 0.15\%^a$ | $10.05 \pm 0.43\%^b$ | $4.44 \pm 0.14\%^c$ | $1.24 \pm 0.02\%^d$ |
| Comparative Example 3 | $33.40 \pm 2.50\%^a$ | $27.60 \pm 0.60\%^b$ | $16.95 \pm 1.34\%^c$ | $9.31 \pm 0.17\%^d$ |
| Comparative Example 4 | $40.69 \pm 1.38\%^a$ | $36.69 \pm 0.86\%^b$ | $25.84 \pm 0.14\%^c$ | $16.51 \pm 0.32\%^d$ |
| Comparative Example 5 | $43.10 \pm 1.42\%^a$ | $39.12 \pm 0.27\%^b$ | $28.73 \pm 2.31\%^c$ | $18.05 \pm 0.14\%^d$ |
| Comparative Example 6 | $40.12 \pm 1.03\%^a$ | $34.26 \pm 0.23\%^b$ | $25.02 \pm 0.13\%^c$ | $16.79 \pm 0.18\%^d$ |

Note:
Different letters of the same index indicated that there were significant differences ($p < 0.05$).

TABLE 18

The performance (the turbidity ($cm^{-1}$)) test results of the oil-in-water nano-emulsions after the thermal sterilization treatment experiment

| Example | New emulsion | Heated at 40° C. for 30 min | Heated at 65° C. for 30 min | Heated at 90° C. for 30 min |
|---|---|---|---|---|
| Example 2 | $328.41 \pm 7.09^a$ | $298.32 \pm 9.44^b$ | $251.87 \pm 0.81^c$ | $167.74 \pm 0.81^d$ |
| Example 3 | $319.03 \pm 4.16^a$ | $305.24 \pm 5.04^b$ | $266.08 \pm 1.31^c$ | $174.13 \pm 2.37^d$ |
| Example 4 | $315.86 \pm 2.44^a$ | $308.73 \pm 0.82^b$ | $274.27 \pm 2.79^c$ | $178.15 \pm 2.93^d$ |
| Comparative Example 1 | $567.61 \pm 7.74^a$ | $532.15 \pm 4.61^b$ | $442.71 \pm 1.74^c$ | $319.66 \pm 1.74^d$ |
| Comparative Example 2 | $521.55 \pm 4.06^a$ | $509.58 \pm 2.19^a$ | $374.54 \pm 8.66^b$ | $258.93 \pm 4.28^c$ |
| Comparative Example 3 | $480.48 \pm 2.46^a$ | $451.31 \pm 4.73^b$ | $343.68 \pm 1.06^c$ | $248.80 \pm 4.89^d$ |
| Comparative Example 4 | $398.80 \pm 9.98^a$ | $364.95 \pm 4.32^b$ | $285.42 \pm 2.14^c$ | $219.32 \pm 3.24^d$ |

TABLE 18-continued

The performance (the turbidity (cm$^{-1}$)) test results of the oil-in-water nano-emulsions after the thermal sterilization treatment experiment

| Example | New emulsion | Heated at 40° C. for 30 min | Heated at 65° C. for 30 min | Heated at 90° C. for 30 min |
|---|---|---|---|---|
| Comparative Example 5 | 367.71 ± 20.87$^a$ | 343.15 ± 8.80$^b$ | 257.40 ± 2.36$^c$ | 187.62 ± 1.39$^d$ |
| Comparative Example 6 | 413.00 ± 4.87$^a$ | 390.28 ± 10.58$^b$ | 342.69 ± 4.23$^c$ | 305.38 ± 1.80$^d$ |

Note:
Different letters of the same index indicated that there were significant differences ($p < 0.05$).

It could be seen from Table 3-Table 18 that the stability of the nano-emulsions could change to different degrees after different treatments (e.g., the storage experiment, the freeze-thaw cycle experiment, and the thermal sterilization treatment experiment). The mean droplet diameter and polydispersity index of the nano-emulsions increased, indicating that the droplet size uniformity of the nano-emulsions reduced. The centrifugal stability constant of the nano-emulsions decreased, and loss (reduction) of the turbidity of the nano-emulsions can be caused. The changes in the mean droplet diameter, polydispersity index, centrifugal stability constant and turbidity reflect the processing stability of the nano-emulsions.

Comparative Example 7

The WPI in step (1) of Example 2 was adjusted to sodium caseinate, the amount ratio of sodium caseinate, Tween 80 and water was 0.5 g:0.5 g:50 mL, and the other steps were the same as those in Example 2, so as to obtain oil-in-water nano-emulsion.

Comparative Example 8

The WPI in step (1) of Example 2 was adjusted to sucrose ester, the amount ratio of sucrose ester, Tween 80 and water was 0.5 g:0.5 g:50 mL, and the other steps were the same as those in Example 2, so as to obtain oil-in-water nano-emulsion.

Comparative Example 9

The Tween 80 in step (1) of Example 2 was adjusted to sodium caseinate, the amount ratio of WPI, sodium caseinate and water was 0.5 g:0.5 g:50 mL, and the other steps were the same as those in Example 2, so as to obtain oil-in-water nano-emulsion.

Comparative Example 10

The Tween 80 in step (1) of Example 2 was adjusted to sucrose ester, the amount ratio of WPI, sucrose ester and water was 0.5 g:0.5 g:50 mL, and the other steps were the same as those in Example 2, so as to obtain oil-in-water nano-emulsion.

The obtained oil-in-water nano-emulsions was tested for performances, and the test results are as follows:

Table 19 shows the performance test results of oil-in-water nano-emulsions prepared by different types of emulsifiers. It could be seen from Table 19 that by adjusting WPI (or Tween 80) to sodium caseinate or sucrose ester, the encapsulation efficiency of ginsenosides Rg3 and CK in the nano-emulsions was lower and the stability was poor, which were not as good as those of the nano-emulsions prepared with WPI and Tween 80.

TABLE 19

The performance test results of oil-in-water nano-emulsions prepared by different types of emulsifiers

| Example | Encapsulation efficiency of ginsenosides Rg3 | Encapsulation efficiency of ginsenosides CK | Mean droplet diameter(nm) | Polydispersity index | Centrifugal stability constant | Turbidity (cm$^{-1}$) |
|---|---|---|---|---|---|---|
| Example 2 | 81.34 ± 0.10%$^a$ | 83.44 ± 0.30%$^a$ | 310.87 ± 1.45$^e$ | 0.17 ± 0.02$^e$ | 53.56 ± 0.48%$^a$ | 328.41 ± 7.09$^e$ |
| Comparative Example 7 | 78.98 ± 2.32%$^b$ | 80.12 ± 2.14%$^b$ | 573.94 ± 9.86$^b$ | 0.22 ± 0.01$^b$ | 18.64 ± 0.85%$^c$ | 482.13 ± 5.19$^b$ |
| Comparative Example 8 | 77.65 ± 1.58%$^c$ | 78.84 ± 1.55%$^c$ | 668.27 ± 13.79$^a$ | 0.23 ± 0.02$^a$ | 21.58 ± 1.03%$^c$ | 525.86 ± 6.43$^a$ |
| Comparative Example 9 | 73.41 ± 0.47%$^e$ | 75.34 ± 0.51%$^e$ | 436.78 ± 5.47$^d$ | 0.20 ± 0.00$^d$ | 38.23 ± 2.21%$^b$ | 405.48 ± 3.07$^d$ |
| Comparative Example 10 | 74.57 ± 0.84%$^d$ | 76.08 ± 0.88%$^d$ | 526.76 ± 8.47$^c$ | 0.21 ± 0.00$^c$ | 35.41 ± 1.96%$^b$ | 446.91 ± 4.25$^c$ |

Note:
Different letters of the same index indicated that there were significant differences ($p < 0.05$).

Comparative Example 11

Heating the WPI solution at 80° C. for 15 min in Example 2 was omitted, and the other steps were the same as those in Example 2, so as to obtain oil-in-water nano-emulsion.

Comparative Example 12

The shearing dispersion at 15000 rpm for 5 min in Example 2 was omitted, and the other steps were the same as those in Example 2, so as to obtain oil-in-water nano-emulsion.

Comparative Example 13

The microfluidization homogenization performed on the coarse emulsion under the pressure of 600 bar for 10 min in Example 2 was omitted, and the other steps were the same as those in Example 2, so as to obtain oil-in-water nano-emulsion.

The obtained oil-in-water nano-emulsions were tested for performances, and the test results are as follows:

Table 20 shows the performance test results of the oil-in-water nano-emulsions prepared under different process conditions. It could be seen from Table 20 that a step in the preparation of the nano-emulsion was omitted, and the encapsulation efficiency of ginsenosides Rg3 and CK in the nano-emulsions prepared under different process conditions was lower and the stability was poor, which were not as good as those of the nano-emulsions prepared under the original process conditions.

TABLE 20

The performance test results of the oil-in-water nano-emulsions prepared under different process conditions

| Example | Encapsulation efficiency of ginsenosides Rg3 | Encapsulation efficiency of ginsenosides CK | Mean droplet diameter (nm) | Polydispersity index | Centrifugal stability constant | Turbidity (cm$^{-1}$) |
|---|---|---|---|---|---|---|
| Example 2 | 81.34 ± 0.10%$^a$ | 83.44 ± 0.30%$^a$ | 310.87 ± 1.45$^c$ | 0.17 ± 0.02$^d$ | 53.56 ± 0.48%$^a$ | 328.41 ± 7.09$^c$ |
| Comparative Example 11 | 76.27 ± 1.17%$^c$ | 78.69 ± 1.34%$^c$ | 381.03 ± 3.52$^c$ | 0.20 ± 0.00$^c$ | 48.76 ± 3.84%$^b$ | 367.94 ± 2.16$^c$ |
| Comparative Example 12 | 78.03 ± 2.09%$^b$ | 79.76 ± 1.71%$^b$ | 749.53 ± 18.62$^b$ | 0.25 ± 0.03$^b$ | 44.92 ± 2.47%$^c$ | 569.35 ± 7.92$^b$ |
| Comparative Example 13 | 75.19 ± 0.98%$^d$ | 77.23 ± 1.02%$^d$ | 1024.36 ± 57.34$^a$ | 0.28 ± 0.04$^a$ | 12.79 ± 0.56%$^d$ | 628.94 ± 9.36$^a$ |

Note:
Different letters of the same index indicated that there were significant differences ($p < 0.05$).

Comparative Example 14

The WPI used in Example 2 was adjusted to WPC (whey protein concentrate), and the other steps were the same as those in Example 2, so as to obtain oil-in-water nano-emulsion.

The obtained oil-in-water nano-emulsion was tested for performances, and the test results are as follows:

TABLE 21

Comparison of WPI/Tween 80 and WPC/Tween 80

| Emulgator | Encapsulation efficiency of ginsenosides Rg3 | Encapsulation efficiency of ginsenosides CK | Mean droplet diameter (nm) | Polydispersity index | Centrifugal stability constant |
|---|---|---|---|---|---|
| WPI(Example 2) | 81.34 ± 0.10%$^a$ | 83.44 ± 0.30%$^a$ | 310.87 ± 1.45$^b$ | 0.17 ± 0.02$^b$ | 53.56 ± 0.48%$^a$ |
| WPC(Comparative Example14) | 75.62 ± 0.49%$^b$ | 78.12 ± 0.83%$^b$ | 386.23 ± 5.17$^a$ | 0.20 ± 0.01$^a$ | 40.08 ± 1.39%$^b$ |

The schematic diagram presenting storage is shown in FIG. 3.

It could be seen from FIG. 3 and Table 21 that the nano-emulsion prepared with the WPC had obvious stratification after storage at 4° C. for 28 days, and its physicochemical properties were relatively poor, which were not as good as those of the nano-emulsion prepared with the WPI.

To sum up, the present disclosure has screened many components, and it is found that only in the technical solution of the present disclosure, when WPI and Tween 80 are used as emulsifiers, and the amount ratio of WPI, Tween 80 and water is 0.5 g:(0.5-0.7) g:50 mL, the nano-emulsion has higher encapsulation efficiency of ginsenosides Rg3 and CK, stronger physicochemical stability, and good processing stability after different treatments. If other kinds of emulsifiers, such as Tween 80 and sodium caseinate, Tween 80 and sucrose ester, WPI and sodium caseinate, and WPI and sucrose ester, are selected, the encapsulation efficiency of the ginsenosides Rg3 and CK in nano-emulsions is lower and the physicochemical stability is poor. If the addition amount is not in accordance with the present disclosure, for example, the addition amount of Tween is 0.1-0.4 g, the encapsulation efficiency of the ginsenosides Rg3 and CK in nano-emulsions is lower and the physicochemical stability is worse than those in nano-emulsions prepared with optimal components. The results of Comparative Example 1 show that the physicochemical stability of nano-emulsion is poor without the addition of Tween 80. The results of Comparative Example 6 show that the encapsulation efficiency of ginsenosides Rg3 and CK in nano-emulsion is lower without the addition of WPI. Not in accordance with the method provided by the present disclosure, such as omitting the heating of the WPI solution at 80° C. for 15 min, omitting the shearing dispersion at the speed of 15000 rpm for 5 min, and omitting the microfluidization homogenization performed on the coarse emulsion under the pressure of 600 bar for 10 min, the encapsulation efficiency of the ginsenosides Rg3 and CK in nano-emulsions is lower and the physicochemical stability is poor.

Therefore, it can be seen from the above examples and comparative examples: the nano-emulsion prepared with WPI and Tween 80 as emulsifiers has higher encapsulation efficiency of ginsenosides Rg3 and CK and stronger physicochemical stability and good processing stability after different treatments. It is the key technical means to control the amount ratio of WPI, Tween 80 and water to be 0.5 g:(0.5-0.7) g:50 mL, which has a great market promotion value.

Although the present disclosure has been disclosed through exemplary examples above, the exemplary examples are not intended to limit the present disclosure, and various changes and modifications can be made by those skilled in the art without departing from the spirit and scope of the present disclosure. Therefore, the scope of protection of the present disclosure shall be as defined by the claims.

What is claimed is:

1. A method to improve the encapsulation efficiency and physicochemical stability of ginsenosides Rg3 and CK nano-emulsion, which comprises:

obtaining an aqueous phase comprising whey protein isolate (WPI), water, and Tween 80, by:
dissolving WPI in water, heating the WPI in water at 80 to 90° C. for 15 to 20 minutes,
cooling the WPI in water to room temperature (25±2° C.) with an ice water bath,
adding Tween 80 to the WPI and water, stirring the WPI, water and Tween 80 at 200 to 400 rpm for 2 to 4 hours, and
mixing the WPI, Tween 80 and water,
resting the WPI, Tween 80, and water at 4° C. for 10 to 12 hours until the WPI, Tween 80, and water is completely hydrated to obtain the aqueous phase;
wherein the ratio of WPI, Tween 80, and water in the aqueous phase is 0.5 g:0.5 g to 0.7 g:50 mL,
obtaining an oil phase comprising a saponin extract with ginsenosides Rg3 and CK and oil by preparing the saponin extract with ginsenosides Rg3 and CK by:
mixing *ginseng* tablets with a citric acid solution with a pH value of 1 to 7,
heating the *ginseng* tablets and citric acid mixture at 130° C. for 1 to 5 hours to obtain the saponin extract containing the minor ginsenosides Rg3 and CK;
mixing the saponin extract containing minor ginsenosides Rg3 and CK with an edible oil selected from the group consisting of: rapeseed oil, soybean oil, sunflower seed oil, and peanut oil, to obtain the oil phase; and
obtaining an oil-in-water nano-emulsion that comprises the minor ginsenosides Rg3 and CK by:
mixing the aqueous phase with the oil phase at a volume ratio of the aqueous phase to the oil phase of 1:1,
performing shearing dispersion of the aqueous phase and oil phase mixture to obtain a coarse emulsion,
subjecting the coarse emulsion to microfluidization homogenization to obtain the oil-in-water nano-emulsion containing the minor ginsenosides Rg3 and CK.

2. The method according to claim 1, wherein the microfluidization homogenization has a shearing dispersion comprising shearing at 15000 rpm to 18000 rpm for 4 to 6 minutes.

3. The method according to claim 1, wherein the microfluidization homogenization comprises cycle homogenization at 600 bar to 800 bar for 10 to 15 minutes.

4. The method according to claim 1, wherein the volume ratio of the saponin extract comprising the minor ginsenosides Rg3 and CK to the edible oil is 4:1.

5. The method according to claim 1,
wherein the ratio of the *ginseng* tablets to the citric acid solution is 1 g:5 to 10 mL;
wherein the preparation of the saponin extract with ginsensosides Rg3 and CK comprises an acid hydrolysis procedure comprising:
heating the *ginseng* tablets with the citric acid solution at 130° C. for 1 hour and a pH value of 2.0, or
heating the *ginseng* tablets with the citric acid solution at 130° C. for 3 to 5 hours at a pH of 3.0 to 7.0.

6. The method according to claim 1, wherein the edible oil comprises sunflower seed oil.

7. An oil-in-water nano-emulsion comprising the ginsenosides Rg3 and CK prepared by the method according to claim 1.

* * * * *